US010760123B2

(12) United States Patent
Amorese et al.

(10) Patent No.: US 10,760,123 B2
(45) Date of Patent: Sep. 1, 2020

(54) SEQUENTIAL SEQUENCING

(71) Applicant: NuGEN Technologies, Inc., San Carlos, CA (US)

(72) Inventors: Doug Amorese, Los Altos, CA (US); Benjamin G. Schroeder, San Mateo, CA (US); Jonathan Scolnick, San Francisco, CA (US)

(73) Assignee: NUGEN TECHNOLOGIES, INC., Redwood City, CA (US)

( * ) Notice: Subject to any disclaimer, the term of this patent is extended or adjusted under 35 U.S.C. 154(b) by 45 days.

(21) Appl. No.: 14/990,339

(22) Filed: Jan. 7, 2016

(65) Prior Publication Data
US 2016/0251712 A1   Sep. 1, 2016

Related U.S. Application Data

(63) Continuation of application No. 14/211,261, filed on Mar. 14, 2014, now abandoned.

(60) Provisional application No. 61/801,600, filed on Mar. 15, 2013.

(51) Int. Cl.
C12Q 1/6874 (2018.01)
G16B 30/00 (2019.01)

(52) U.S. Cl.
CPC .......... *C12Q 1/6874* (2013.01); *G16B 30/00* (2019.02)

(58) Field of Classification Search
CPC ...... C12Q 1/6874; C12Q 1/6869; G06F 19/22
See application file for complete search history.

(56) References Cited

U.S. PATENT DOCUMENTS

| 4,362,867 A | 12/1982 | Paddock |
| 4,458,066 A | 7/1984 | Caruthers et al. |
| 4,469,863 A | 9/1984 | Ts'o et al. |
| 4,582,877 A | 4/1986 | Fairchok et al. |
| 4,876,187 A | 10/1989 | Duck et al. |

(Continued)

FOREIGN PATENT DOCUMENTS

| CA | 2444926 A1 | 11/2002 |
| CN | 1661102 A | 8/2005 |

(Continued)

OTHER PUBLICATIONS

Shendure, J. et al., Science, vol. 309, pp. 1728-1732, and supplementary material, pp. 1-41 (2005).*

(Continued)

*Primary Examiner* — Teresa E Strzelecka
(74) *Attorney, Agent, or Firm* — Brown Rudnick LLP; Thomas C. Meyers

(57) ABSTRACT

The present invention provides improved methods, compositions and kits for short read next generation sequencing (NGS). The methods, compositions and kits of the present invention enable phasing of two or more nucleic acid sequences in a sample, i.e. determining whether the nucleic acid sequences (typically comprising regions of sequence variation) are located on the same chromosome and/or the same chromosomal fragment. Phasing information is obtained by performing multiple, successive sequencing reactions from the same immobilized nucleic acid template. The methods, compositions and kits provided herein are useful, for example, for haplotyping, SNP phasing, or for determining downstream exons in RNA-seq.

11 Claims, 2 Drawing Sheets

Read 1 oligo hybridizes and sequences all clusters (illumina sequencing). The two clusters on the right represent DNA from a gene and its pseudogene. One cluster (far right) has a mutation in read 1, but it is not clear which is the gene and which is the pseudogene.

Melt away read 1. Flow in a pool of oligonucleotide primers (dark gray and medium gray) complementary to DNAs contained in some clusters on the flow cell. Read 2 sequencing is then performed A mated pair of sequences now exist. The two heavy lines/sequences can now be distinguished from each other by the cytosine in read two. In this scenario, that cytosine shows that the right most sequence is the pseudogene and so there is no concern about the mutation found in read 1.

(56) References Cited

U.S. PATENT DOCUMENTS

| | | |
|---|---|---|
| 4,925,065 A | 5/1990 | Golias |
| 4,935,357 A | 6/1990 | Szybalski |
| 4,942,124 A | 7/1990 | Church |
| 4,988,617 A | 1/1991 | Landegren et al. |
| 4,996,143 A | 2/1991 | Heller et al. |
| 5,011,769 A | 4/1991 | Duck et al. |
| 5,034,506 A | 7/1991 | Summerton et al. |
| 5,035,996 A | 7/1991 | Hartley |
| 5,043,272 A | 8/1991 | Hartley |
| 5,082,830 A | 1/1992 | Brakel et al. |
| 5,090,591 A | 2/1992 | Long |
| 5,130,238 A | 7/1992 | Malek et al. |
| 5,169,766 A | 12/1992 | Schuster et al. |
| 5,171,534 A | 12/1992 | Smith et al. |
| 5,194,370 A | 3/1993 | Berninger et al. |
| 5,216,141 A | 6/1993 | Benner |
| 5,234,809 A | 8/1993 | Boom et al. |
| 5,235,033 A | 8/1993 | Summerton et al. |
| 5,242,794 A | 9/1993 | Whiteley et al. |
| 5,384,242 A | 1/1995 | Oakes |
| 5,386,023 A | 1/1995 | Sanghvi et al. |
| 5,399,491 A | 3/1995 | Kucian et al. |
| 5,409,818 A | 4/1995 | Davey et al. |
| 5,418,149 A | 5/1995 | Gelfand et al. |
| 5,422,271 A | 6/1995 | Chen et al. |
| 5,427,929 A | 6/1995 | Richards et al. |
| 5,480,784 A | 1/1996 | Kacian et al. |
| 5,494,810 A | 2/1996 | Barany et al. |
| 5,508,169 A | 4/1996 | Deugau et al. |
| 5,508,178 A | 4/1996 | Rose et al. |
| 5,510,270 A | 4/1996 | Fodor et al. |
| 5,525,471 A | 6/1996 | Zeng |
| 5,545,522 A | 8/1996 | Van Gelder et al. |
| 5,554,516 A | 9/1996 | Kacian et al. |
| 5,554,517 A | 9/1996 | Davey et al. |
| 5,556,752 A | 9/1996 | Lockhart et al. |
| 5,565,340 A | 10/1996 | Chenchik et al. |
| 5,573,913 A | 11/1996 | Rosemeyer et al. |
| 5,578,832 A | 11/1996 | Trulson et al. |
| 5,589,339 A | 12/1996 | Hampson et al. |
| 5,602,240 A | 2/1997 | De Mesmaeker et al. |
| 5,637,684 A | 6/1997 | Cook et al. |
| 5,641,658 A | 6/1997 | Adams et al. |
| 5,644,048 A | 7/1997 | Yau et al. |
| 5,665,549 A | 9/1997 | Pinkel et al. |
| 5,667,976 A | 9/1997 | Van Ness et al. |
| 5,667,979 A | 9/1997 | Berrens |
| 5,679,512 A | 10/1997 | Laney et al. |
| 5,681,726 A | 10/1997 | Huse et al. |
| 5,683,879 A | 11/1997 | Laney et al. |
| 5,688,648 A | 11/1997 | Mathies et al. |
| 5,705,628 A | 1/1998 | Hawkins |
| 5,708,154 A | 1/1998 | Smith et al. |
| 5,710,028 A | 1/1998 | Eyal et al. |
| 5,712,126 A | 1/1998 | Weissman et al. |
| 5,716,785 A | 2/1998 | Van Gelder et al. |
| 5,726,329 A | 3/1998 | Jones et al. |
| 5,750,341 A | 5/1998 | Macevicz |
| 5,759,822 A | 6/1998 | Chenchik et al. |
| 5,763,178 A | 6/1998 | Chirikjian et al. |
| 5,789,206 A | 8/1998 | Tavtigian et al. |
| 5,824,517 A | 10/1998 | Cleuziat et al. |
| 5,824,518 A | 10/1998 | Kacian et al. |
| 5,837,832 A | 11/1998 | Chee et al. |
| 5,876,976 A | 3/1999 | Richards et al. |
| 5,882,867 A | 3/1999 | Ullman et al. |
| 5,888,779 A | 3/1999 | Kacian et al. |
| 5,888,819 A | 3/1999 | Goelet et al. |
| 5,945,313 A | 8/1999 | Hartley et al. |
| 5,952,176 A | 9/1999 | McCarthy et al. |
| 5,958,681 A | 9/1999 | Wetmur et al. |
| 5,965,409 A | 10/1999 | Pardee et al. |
| 5,969,119 A | 10/1999 | Macevicz |
| 5,972,618 A | 10/1999 | Bloch |
| 6,004,744 A | 12/1999 | Goelet et al. |
| 6,004,745 A | 12/1999 | Arnold, Jr. et al. |
| 6,027,889 A | 2/2000 | Barany et al. |
| 6,027,923 A | 2/2000 | Wallace |
| 6,030,774 A | 2/2000 | Laney et al. |
| 6,037,152 A | 3/2000 | Richards et al. |
| 6,056,661 A | 5/2000 | Schmidt |
| 6,077,674 A | 6/2000 | Schleifer et al. |
| 6,087,103 A | 7/2000 | Burmer |
| 6,090,553 A | 7/2000 | Matson |
| 6,090,591 A | 7/2000 | Berg et al. |
| 6,107,023 A | 8/2000 | Reyes et al. |
| 6,110,709 A | 8/2000 | Ausubel et al. |
| 6,150,112 A | 11/2000 | Weissman et al. |
| 6,159,685 A | 12/2000 | Pinkel et al. |
| 6,160,105 A | 12/2000 | Cunningham et al. |
| 6,169,194 B1 | 1/2001 | Thompson et al. |
| 6,172,208 B1 | 1/2001 | Cook |
| 6,174,680 B1 | 1/2001 | Makrigiorgos |
| 6,180,338 B1 | 1/2001 | Adams |
| 6,190,865 B1 | 2/2001 | Jendrisak et al. |
| 6,194,211 B1 | 2/2001 | Richards et al. |
| 6,197,501 B1 | 3/2001 | Cremer et al. |
| 6,197,557 B1 | 3/2001 | Makarov et al. |
| 6,210,891 B1 | 4/2001 | Nyren et al. |
| 6,225,109 B1 | 5/2001 | Juncosa et al. |
| 6,225,451 B1 | 5/2001 | Ballinger et al. |
| 6,232,104 B1 | 5/2001 | Lishanski et al. |
| 6,251,639 B1 | 6/2001 | Kurn |
| 6,262,490 B1 | 7/2001 | Hsu et al. |
| 6,270,961 B1 | 8/2001 | Drmanac |
| 6,280,935 B1 | 8/2001 | Macevicz |
| 6,287,766 B1 | 9/2001 | Nolan et al. |
| 6,287,825 B1 | 9/2001 | Weissman et al. |
| 6,291,170 B1 | 9/2001 | Van Gelder et al. |
| 6,306,365 B1 | 10/2001 | Ruoslahti et al. |
| 6,306,597 B1 | 10/2001 | Macevicz |
| 6,309,843 B1 | 10/2001 | Timms |
| 6,326,142 B1 | 12/2001 | Royer |
| 6,335,167 B1 | 1/2002 | Pinkel et al. |
| 6,339,147 B1 | 1/2002 | Luktanov et al. |
| 6,440,705 B1 | 8/2002 | Stanton, Jr. et al. |
| 6,449,562 B1 | 9/2002 | Chandler et al. |
| 6,582,938 B1 | 6/2003 | Su et al. |
| 6,670,461 B1 | 12/2003 | Wengel et al. |
| 6,686,156 B2 | 2/2004 | Kurn |
| 6,692,918 B2 | 2/2004 | Kurn |
| 6,770,748 B2 | 8/2004 | Imanishi et al. |
| 6,777,180 B1 | 8/2004 | Fisher et al. |
| 6,794,499 B2 | 9/2004 | Wengel et al. |
| 6,815,164 B2 | 11/2004 | Kurn |
| 6,815,167 B2 | 11/2004 | Crothers et al. |
| 6,825,011 B1 | 11/2004 | Romantchikov |
| 6,833,246 B2 | 12/2004 | Balasubramanian |
| 6,849,404 B2 | 2/2005 | Park et al. |
| 6,858,413 B2 | 2/2005 | Kurn |
| 6,913,884 B2 | 7/2005 | Stuelpnagel et al. |
| 6,917,726 B2 | 7/2005 | Levene et al. |
| 6,924,104 B2 | 8/2005 | Weissman et al. |
| 6,946,251 B2 | 9/2005 | Kurn |
| 7,001,724 B1 | 2/2006 | Greenfield |
| 7,033,764 B2 | 4/2006 | Korlach et al. |
| 7,048,481 B2 | 5/2006 | Sugata et al. |
| 7,052,847 B2 | 5/2006 | Korlach et al. |
| 7,056,676 B2 | 6/2006 | Korlach et al. |
| 7,056,716 B2 | 6/2006 | Potter et al. |
| 7,060,441 B2 | 6/2006 | Bourget et al. |
| 7,094,536 B2 | 8/2006 | Kurn |
| 7,115,400 B1 | 10/2006 | Adessi et al. |
| 7,170,050 B2 | 1/2007 | Turner |
| 7,175,982 B1 | 2/2007 | McCarthy et al. |
| 7,176,025 B2 | 2/2007 | Kurn et al. |
| 7,189,512 B2 | 3/2007 | Porat et al. |
| 7,211,390 B2 | 5/2007 | Rothberg et al. |
| 7,232,656 B2 | 6/2007 | Balasubramanian et al. |
| 7,244,559 B2 | 7/2007 | Rothberg et al. |
| 7,244,567 B2 | 7/2007 | Chen et al. |
| 7,264,929 B2 | 9/2007 | Rothberg et al. |
| 7,273,730 B2 | 9/2007 | Du Breuil |
| 7,276,720 B2 | 10/2007 | Ulmer |

(56) References Cited

U.S. PATENT DOCUMENTS

| | | |
|---|---|---|
| 7,294,461 B2 | 11/2007 | Kurn |
| 7,300,755 B1 | 11/2007 | Petersdorf et al. |
| 7,302,146 B2 | 11/2007 | Turner et al. |
| 7,313,308 B2 | 12/2007 | Turner et al. |
| 7,315,019 B2 | 1/2008 | Turner et al. |
| 7,323,305 B2 | 1/2008 | Leamon et al. |
| 7,335,762 B2 | 2/2008 | Rothberg et al. |
| 7,351,557 B2 | 4/2008 | Kurn |
| 7,354,717 B2 | 4/2008 | Kurn |
| 7,361,466 B2 | 4/2008 | Korlach et al. |
| 7,361,468 B2 | 4/2008 | Liu et al. |
| 7,402,386 B2 | 7/2008 | Kurn et al. |
| 7,405,281 B2 | 7/2008 | Xu et al. |
| 7,414,117 B2 | 8/2008 | Saito et al. |
| 7,416,844 B2 | 8/2008 | Korlach et al. |
| 7,462,452 B2 | 12/2008 | Williams et al. |
| 7,462,468 B1 | 12/2008 | Williams et al. |
| 7,476,503 B2 | 1/2009 | Turner et al. |
| 7,476,504 B2 | 1/2009 | Turner |
| 7,491,498 B2 | 2/2009 | Lapidus et al. |
| 7,501,245 B2 | 3/2009 | Quake et al. |
| 7,579,153 B2 | 8/2009 | Brenner et al. |
| 7,704,687 B2 | 4/2010 | Wang et al. |
| 7,741,463 B2 | 6/2010 | Gormley et al. |
| 7,771,934 B2 | 8/2010 | Kurn |
| 7,771,946 B2 | 8/2010 | Kurn |
| 7,803,550 B2 | 9/2010 | Makarov et al. |
| 7,846,666 B2 | 12/2010 | Kum et al. |
| 7,846,733 B2 | 12/2010 | Kurn |
| 7,867,703 B2 | 1/2011 | Sampson et al. |
| 7,939,258 B2 | 5/2011 | Kurn et al. |
| 7,948,015 B2 | 5/2011 | Rothberg et al. |
| 7,985,565 B2 | 7/2011 | Mayer et al. |
| 8,017,335 B2 | 9/2011 | Smith |
| 8,034,568 B2 | 10/2011 | Kurn et al. |
| 8,053,192 B2 | 11/2011 | Bignell et al. |
| 8,071,311 B2 | 12/2011 | Kurn |
| 8,143,001 B2 | 3/2012 | Kurn et al. |
| 8,209,130 B1 | 6/2012 | Kennedy et al. |
| 8,334,116 B2 | 12/2012 | Kurn |
| 8,465,950 B2 | 6/2013 | Kurn et al. |
| 8,492,095 B2 | 7/2013 | Kurn |
| 8,512,956 B2 | 8/2013 | Kurn et al. |
| 8,551,709 B2 | 10/2013 | Kurn et al. |
| 8,852,867 B2 | 10/2014 | Kurn et al. |
| 8,999,677 B1 | 4/2015 | Soldatov et al. |
| 9,175,325 B2 | 11/2015 | Kurn et al. |
| 9,175,336 B2 | 11/2015 | Soldatov et al. |
| 9,181,582 B2 | 11/2015 | Kurn |
| 9,206,418 B2 | 12/2015 | Armour |
| 9,248,076 B2 | 2/2016 | Sullivan et al. |
| 9,546,399 B2 | 1/2017 | Amorese et al. |
| 9,650,628 B2 | 5/2017 | Amorese et al. |
| 9,702,004 B2 | 7/2017 | Van Eijk et al. |
| 9,745,627 B2 | 8/2017 | van Eijk et al. |
| 9,896,721 B2 | 2/2018 | Van Eijk et al. |
| 2001/0000077 A1 | 3/2001 | Engelhardt et al. |
| 2001/0031739 A1 | 10/2001 | Dare |
| 2001/0034048 A1 | 10/2001 | Kurn |
| 2001/0041334 A1 | 11/2001 | Rashtchian et al. |
| 2002/0028447 A1 | 3/2002 | Li et al. |
| 2002/0058270 A1 | 5/2002 | Kurn |
| 2002/0115088 A1 | 8/2002 | Kurn |
| 2002/0150919 A1 | 10/2002 | Weissmann et al. |
| 2002/0155451 A1 | 10/2002 | Makrigiorgos |
| 2002/0164628 A1 | 11/2002 | Kurn |
| 2002/0164634 A1 | 11/2002 | Patil et al. |
| 2002/0197639 A1 | 12/2002 | Shia et al. |
| 2003/0017591 A1 | 1/2003 | Kurn |
| 2003/0022207 A1 | 1/2003 | Balasubramanian et al. |
| 2003/0082543 A1 | 5/2003 | Su et al. |
| 2003/0087251 A1 | 5/2003 | Kurn |
| 2003/0119150 A1 | 6/2003 | Ankenbauer et al. |
| 2003/0143555 A1 | 7/2003 | Bourget et al. |
| 2003/0175780 A1 | 9/2003 | Jones |
| 2003/0180779 A1 | 9/2003 | Lofton-Day et al. |
| 2003/0186234 A1 | 10/2003 | Kurn |
| 2003/0207279 A1 | 11/2003 | Crothers et al. |
| 2003/0211616 A1 | 11/2003 | Leong |
| 2003/0215926 A1 | 11/2003 | Kurn et al. |
| 2003/0224439 A1 | 12/2003 | Lafferty et al. |
| 2003/0232348 A1 | 12/2003 | Jones et al. |
| 2004/0002371 A1 | 1/2004 | Paquin et al. |
| 2004/0005614 A1 | 1/2004 | Kurn et al. |
| 2004/0023271 A1 | 2/2004 | Kurn et al. |
| 2004/0115815 A1 | 6/2004 | Li et al. |
| 2004/0137456 A1 | 7/2004 | Yokota et al. |
| 2004/0161742 A1 | 8/2004 | Dean et al. |
| 2004/0203019 A1 | 10/2004 | Kurn |
| 2004/0203025 A1 | 10/2004 | Kurn |
| 2004/0248153 A1 | 12/2004 | Dear et al. |
| 2005/0003441 A1 | 1/2005 | Kurn |
| 2005/0014192 A1 | 1/2005 | Kurn |
| 2005/0019793 A1 | 1/2005 | Kurn et al. |
| 2005/0059048 A1 | 3/2005 | Gunderson et al. |
| 2005/0064456 A1 | 3/2005 | Kurn |
| 2005/0123956 A1 | 6/2005 | Blume et al. |
| 2005/0136417 A1 | 6/2005 | Cole et al. |
| 2005/0142577 A1 | 6/2005 | Jones et al. |
| 2005/0191656 A1 | 9/2005 | Drmanac et al. |
| 2005/0191682 A1 | 9/2005 | Barone et al. |
| 2005/0208538 A1 | 9/2005 | Kurn et al. |
| 2006/0008824 A1 | 1/2006 | Ronaghi et al. |
| 2006/0014182 A1 | 1/2006 | Kurn |
| 2006/0024678 A1 | 2/2006 | Buzby |
| 2006/0024711 A1 | 2/2006 | Lapidus et al. |
| 2006/0035274 A1 | 2/2006 | Dong |
| 2006/0046251 A1 | 3/2006 | Sampson et al. |
| 2006/0051789 A1 | 3/2006 | Kazakov et al. |
| 2006/0068415 A1 | 3/2006 | Jones et al. |
| 2006/0134633 A1 | 6/2006 | Chen et al. |
| 2006/0216724 A1 | 9/2006 | Christians et al. |
| 2006/0263789 A1 | 11/2006 | Kincaid |
| 2006/0281082 A1 | 12/2006 | Zhu |
| 2006/0286566 A1 | 12/2006 | Lapidus et al. |
| 2006/0292597 A1 | 12/2006 | Shapero et al. |
| 2007/0031857 A1 | 2/2007 | Makarov et al. |
| 2007/0134128 A1 | 6/2007 | Korlach |
| 2007/0141604 A1 | 6/2007 | Gormley et al. |
| 2007/0224607 A1 | 9/2007 | Morgan et al. |
| 2007/0224613 A1 | 9/2007 | Strathmann |
| 2007/0231823 A1 | 10/2007 | McKernan et al. |
| 2007/0238122 A1 | 10/2007 | Allbritton et al. |
| 2007/0263045 A1 | 11/2007 | Okazawa |
| 2008/0038727 A1 | 2/2008 | Spier |
| 2008/0087826 A1 | 4/2008 | Harris et al. |
| 2008/0103058 A1 | 5/2008 | Siddiqi |
| 2008/0131937 A1 | 6/2008 | Schroeder |
| 2008/0160580 A1 | 7/2008 | Adessi et al. |
| 2008/0176311 A1 | 7/2008 | Kurn |
| 2008/0182300 A1 | 7/2008 | Kurn |
| 2008/0194413 A1 | 8/2008 | Albert |
| 2008/0194416 A1 | 8/2008 | Chen |
| 2008/0206764 A1 | 8/2008 | Williams et al. |
| 2008/0213770 A1 | 9/2008 | Williams et al. |
| 2008/0217246 A1 | 9/2008 | Benn et al. |
| 2008/0241831 A1 | 10/2008 | Fan et al. |
| 2008/0242560 A1 | 10/2008 | Gunderson et al. |
| 2008/0286795 A1 | 11/2008 | Kawashima et al. |
| 2009/0011959 A1 | 1/2009 | Costa et al. |
| 2009/0024331 A1 | 1/2009 | Tomaney et al. |
| 2009/0026082 A1 | 1/2009 | Rothberg et al. |
| 2009/0029385 A1 | 1/2009 | Christians et al. |
| 2009/0036663 A1 | 2/2009 | Kurn |
| 2009/0061425 A1 | 3/2009 | Lo et al. |
| 2009/0061439 A1 | 3/2009 | Buzby |
| 2009/0068645 A1 | 3/2009 | Sibson |
| 2009/0068655 A1 | 3/2009 | Williams |
| 2009/0068709 A1 | 3/2009 | Kurn et al. |
| 2009/0105081 A1 | 4/2009 | Rodesch et al. |
| 2009/0117573 A1 | 5/2009 | Fu et al. |
| 2009/0117621 A1 | 5/2009 | Boutell et al. |
| 2009/0123923 A1 | 5/2009 | Yamamoto et al. |
| 2009/0124514 A1 | 5/2009 | Fu et al. |

(56) References Cited

U.S. PATENT DOCUMENTS

| | | |
|---|---|---|
| 2009/0127589 A1 | 5/2009 | Rothberg et al. |
| 2009/0130721 A1 | 5/2009 | Kurn et al. |
| 2009/0203085 A1 | 8/2009 | Kurn et al. |
| 2009/0203531 A1 | 8/2009 | Kurn et al. |
| 2009/0233802 A1 | 9/2009 | Bignell et al. |
| 2009/0233804 A1 | 9/2009 | Kurn et al. |
| 2009/0239232 A1 | 9/2009 | Kurn et al. |
| 2009/0275486 A1 | 11/2009 | Kurn et al. |
| 2009/0280538 A1 | 11/2009 | Patel et al. |
| 2009/0298075 A1 | 12/2009 | Travers et al. |
| 2010/0015666 A1 | 1/2010 | Brenner et al. |
| 2010/0021973 A1 | 1/2010 | Makarov et al. |
| 2010/0022403 A1 | 1/2010 | Kurn et al. |
| 2010/0029511 A1 | 2/2010 | Raymond et al. |
| 2010/0081174 A1 | 4/2010 | Dunn |
| 2010/0105052 A1 | 4/2010 | Drmanac et al. |
| 2010/0113296 A1 | 5/2010 | Myerson |
| 2010/0129879 A1 | 5/2010 | Ach et al. |
| 2010/0137143 A1 | 6/2010 | Rothberg et al. |
| 2010/0159559 A1 | 6/2010 | Kurn et al. |
| 2010/0167954 A1 | 7/2010 | Earnshaw et al. |
| 2010/0173394 A1 | 7/2010 | Colston, Jr. et al. |
| 2010/0203597 A1 | 8/2010 | Chen et al. |
| 2010/0267043 A1 | 10/2010 | Braverman et al. |
| 2010/0273219 A1 | 10/2010 | May et al. |
| 2010/0311066 A1 | 12/2010 | Kurn |
| 2010/0323348 A1 | 12/2010 | Hamady et al. |
| 2011/0009276 A1 | 1/2011 | Vermaas et al. |
| 2011/0015096 A1 | 1/2011 | Chiu |
| 2011/0039732 A1 | 2/2011 | Raymond et al. |
| 2011/0104785 A1 | 5/2011 | Vaidyanathan et al. |
| 2011/0105364 A1 | 5/2011 | Kurn |
| 2011/0129827 A1 | 6/2011 | Causey et al. |
| 2011/0189679 A1 | 8/2011 | Kurn et al. |
| 2011/0224105 A1 | 9/2011 | Kurn et al. |
| 2011/0288780 A1 | 11/2011 | Rabinowitz et al. |
| 2011/0294132 A1 | 12/2011 | Kurn et al. |
| 2011/0319290 A1 | 12/2011 | Raymond et al. |
| 2012/0003657 A1 | 1/2012 | Myllykangas et al. |
| 2012/0028310 A1 | 2/2012 | Kurn et al. |
| 2012/0045797 A1 | 2/2012 | Kurn et al. |
| 2012/0071331 A1 | 3/2012 | Casbon et al. |
| 2012/0074925 A1 | 3/2012 | Oliver |
| 2012/0102054 A1 | 4/2012 | Popescu et al. |
| 2012/0107811 A1 | 5/2012 | Kelso et al. |
| 2012/0122701 A1 | 5/2012 | Ryan et al. |
| 2012/0149068 A1 | 6/2012 | Kurn et al. |
| 2012/0156728 A1 | 6/2012 | Li et al. |
| 2012/0157322 A1 | 6/2012 | Myllykangas et al. |
| 2012/0190587 A1 | 7/2012 | Kurn et al. |
| 2012/0208705 A1 | 8/2012 | Steemers et al. |
| 2012/0220483 A1 | 8/2012 | Kurn et al. |
| 2012/0220494 A1 | 8/2012 | Samuels et al. |
| 2012/0237943 A1 | 9/2012 | Soldatov et al. |
| 2012/0238738 A1 | 9/2012 | Hendrickson |
| 2012/0245041 A1 | 9/2012 | Brenner et al. |
| 2012/0252682 A1 | 10/2012 | Zhou et al. |
| 2012/0270212 A1 | 10/2012 | Rabinowitz et al. |
| 2012/0283145 A1 | 11/2012 | Wang |
| 2012/0289426 A1 | 11/2012 | Roos et al. |
| 2012/0309002 A1 | 12/2012 | Link |
| 2013/0005585 A1 | 1/2013 | Anderson et al. |
| 2013/0059738 A1 | 3/2013 | Leamon et al. |
| 2013/0231253 A1 | 9/2013 | Amorese et al. |
| 2014/0038188 A1 | 2/2014 | Kurn |
| 2014/0038236 A1 | 2/2014 | Kurn et al. |
| 2014/0065692 A1 | 3/2014 | Kurn et al. |
| 2014/0274729 A1 | 9/2014 | Kurn et al. |
| 2014/0274731 A1 | 9/2014 | Raymond et al. |
| 2014/0274738 A1 | 9/2014 | Amorese et al. |
| 2014/0303000 A1 | 10/2014 | Armour |
| 2014/0378345 A1 | 12/2014 | Hindson et al. |
| 2015/0004600 A1 | 1/2015 | Wang et al. |
| 2015/0001396 A1 | 1/2015 | Schroeder et al. |
| 2015/0017635 A1 | 1/2015 | Myllykangas et al. |
| 2015/0037790 A1 | 2/2015 | Fox et al. |
| 2015/0101595 A1 | 4/2015 | Hancock et al. |
| 2015/0133319 A1 | 5/2015 | Fu et al. |
| 2015/0284769 A1 | 10/2015 | Schroeder |
| 2015/0299767 A1 | 10/2015 | Armour et al. |
| 2015/0299784 A1 | 10/2015 | Fan et al. |
| 2015/0299812 A1 | 10/2015 | Talasaz |
| 2016/0016140 A1 | 1/2016 | Jovanovich et al. |
| 2016/0122756 A1 | 5/2016 | Armour |
| 2016/0130576 A1 | 5/2016 | Armour |
| 2016/0153039 A1 | 6/2016 | Amorese et al. |
| 2016/0203259 A1 | 7/2016 | Scolnick et al. |
| 2016/0220994 A1 | 8/2016 | Wright |
| 2016/0251711 A1 | 9/2016 | Amorese et al. |
| 2016/0265042 A1 | 9/2016 | Schroeder et al. |
| 2016/0275240 A1 | 9/2016 | Huelga et al. |
| 2016/0296930 A1 | 10/2016 | Matear et al. |

FOREIGN PATENT DOCUMENTS

| | | |
|---|---|---|
| CN | 101565746 A | 10/2009 |
| CN | 105890722 A | 8/2016 |
| EP | 0365627 B1 | 5/1990 |
| EP | 0329822 B1 | 6/1994 |
| EP | 0667393 A2 | 8/1995 |
| EP | 0667393 A3 | 11/1995 |
| EP | 1071811 B1 | 3/2002 |
| EP | 0843735 B1 | 7/2002 |
| EP | 2272976 A1 | 1/2011 |
| EP | 2322612 A1 | 5/2011 |
| EP | 2451973 A1 | 5/2012 |
| EP | 2511381 A1 | 10/2012 |
| EP | 1929039 B2 | 11/2013 |
| WO | 89/09284 A1 | 10/1989 |
| WO | WO 92/07951 A1 | 5/1992 |
| WO | WO 93/18052 A1 | 9/1993 |
| WO | WO 94/16090 A1 | 7/1994 |
| WO | WO 96/40998 A1 | 12/1996 |
| WO | WO 97/12061 A1 | 4/1997 |
| WO | WO 97/25416 A2 | 7/1997 |
| WO | WO 97/25416 A3 | 10/1997 |
| WO | WO 98/06736 A1 | 2/1998 |
| WO | WO 98/38296 A1 | 9/1998 |
| WO | WO 98/44151 A1 | 10/1998 |
| WO | WO 99/10540 A1 | 3/1999 |
| WO | WO 99/11819 A1 | 3/1999 |
| WO | WO 99/42618 A1 | 8/1999 |
| WO | WO 00/08208 A2 | 2/2000 |
| WO | WO 2000/09756 A1 | 2/2000 |
| WO | WO 00/08208 A3 | 5/2000 |
| WO | WO 00/018957 A1 | 6/2000 |
| WO | 2000/043531 A2 | 7/2000 |
| WO | WO 00/39345 A1 | 7/2000 |
| WO | WO 00/52191 A1 | 9/2000 |
| WO | WO 2000/55364 A2 | 9/2000 |
| WO | WO 00/70039 A1 | 11/2000 |
| WO | WO 01/20035 A2 | 3/2001 |
| WO | WO 01/23613 A1 | 4/2001 |
| WO | WO 01/46464 A1 | 6/2001 |
| WO | WO 01/57248 A2 | 8/2001 |
| WO | WO 01/64952 A2 | 9/2001 |
| WO | WO 2000/55364 A3 | 10/2001 |
| WO | WO 01/20035 A3 | 12/2001 |
| WO | WO 02/00938 A2 | 1/2002 |
| WO | WO 01/57248 A3 | 2/2002 |
| WO | WO 02/28876 A2 | 4/2002 |
| WO | WO 02/29117 A2 | 4/2002 |
| WO | WO 02/36821 A2 | 5/2002 |
| WO | WO 02/48402 A2 | 6/2002 |
| WO | WO 02/28876 A3 | 8/2002 |
| WO | WO 02/060318 A2 | 8/2002 |
| WO | WO 02/072772 A2 | 9/2002 |
| WO | WO 02/072773 A2 | 9/2002 |
| WO | WO 02/072773 A3 | 9/2002 |
| WO | WO 02/081753 A1 | 10/2002 |
| WO | WO 02/090584 A2 | 11/2002 |
| WO | WO 01/64952 A3 | 12/2002 |
| WO | 03/004690 A2 | 1/2003 |
| WO | WO 2003/002736 A2 | 1/2003 |

(56) References Cited

FOREIGN PATENT DOCUMENTS

| | | |
|---|---|---|
| WO | WO 2003/012118 A1 | 2/2003 |
| WO | WO 02/36821 A3 | 3/2003 |
| WO | WO 03/027259 A2 | 4/2003 |
| WO | WO 02/00938 A3 | 8/2003 |
| WO | WO 02/29117 A3 | 8/2003 |
| WO | WO 02/072772 A3 | 9/2003 |
| WO | WO 02/090584 A3 | 9/2003 |
| WO | WO 03/078645 A2 | 9/2003 |
| WO | WO 02/060318 A3 | 10/2003 |
| WO | WO 03/083435 A2 | 10/2003 |
| WO | WO 03/027259 A3 | 12/2003 |
| WO | WO 03/106642 A2 | 12/2003 |
| WO | WO 03/083435 A3 | 2/2004 |
| WO | WO 03/078645 A3 | 3/2004 |
| WO | WO 02/48402 A3 | 4/2004 |
| WO | 2004/070007 A2 | 8/2004 |
| WO | WO 04/011665 A2 | 9/2004 |
| WO | WO 2004/092418 A2 | 10/2004 |
| WO | WO 03/106642 A3 | 11/2004 |
| WO | 2005/003375 A2 | 1/2005 |
| WO | 2005/003381 A1 | 1/2005 |
| WO | 2005/038427 A2 | 4/2005 |
| WO | WO 04/011665 A3 | 7/2005 |
| WO | WO 2005/065321 A2 | 7/2005 |
| WO | WO 2006/081222 A2 | 8/2006 |
| WO | WO 2006/086668 A2 | 8/2006 |
| WO | 2006/137733 A1 | 12/2006 |
| WO | WO 2006/081222 A3 | 2/2007 |
| WO | WO 2007/018601 A1 | 2/2007 |
| WO | WO 2007/019444 A2 | 2/2007 |
| WO | WO 2007/030759 A2 | 3/2007 |
| WO | 2007/037678 A2 | 4/2007 |
| WO | WO 2007/052006 A1 | 5/2007 |
| WO | WO 2007/057652 A1 | 5/2007 |
| WO | 2007/073165 A1 | 6/2007 |
| WO | WO 2007/030759 A3 | 6/2007 |
| WO | WO 2007/136717 A1 | 11/2007 |
| WO | WO 2008/005459 A2 | 1/2008 |
| WO | WO 2008/005459 A3 | 2/2008 |
| WO | WO 2008/015396 A2 | 2/2008 |
| WO | WO 2008/033442 A2 | 3/2008 |
| WO | 2008/093098 A2 | 8/2008 |
| WO | WO 2008/115185 A2 | 9/2008 |
| WO | WO 2008/033442 A3 | 10/2008 |
| WO | 2008150432 A1 | 12/2008 |
| WO | WO 2008/115185 A3 | 12/2008 |
| WO | WO 2009/053039 A1 | 4/2009 |
| WO | WO 2005/065321 A3 | 5/2009 |
| WO | WO 2009/102878 A2 | 8/2009 |
| WO | WO 2009/102896 A2 | 8/2009 |
| WO | WO 2009/112844 A1 | 9/2009 |
| WO | WO 2009/117698 A2 | 9/2009 |
| WO | WO 2009/120372 A2 | 10/2009 |
| WO | WO 2009/120374 A2 | 10/2009 |
| WO | WO 2009/120374 A3 | 12/2009 |
| WO | WO 2009/120372 A3 | 1/2010 |
| WO | WO 2010/003153 A2 | 1/2010 |
| WO | WO 2010/030683 A1 | 3/2010 |
| WO | WO 2010/039991 A2 | 4/2010 |
| WO | WO 2010/063711 A1 | 6/2010 |
| WO | WO 2010/064893 A1 | 6/2010 |
| WO | WO 2010/085715 A1 | 7/2010 |
| WO | 2010/091246 A2 | 8/2010 |
| WO | WO 2010/115154 A1 | 10/2010 |
| WO | WO 2010/129937 A2 | 11/2010 |
| WO | WO 2011/003630 A1 | 1/2011 |
| WO | WO 2011/009941 A1 | 1/2011 |
| WO | WO 2011/019964 A1 | 2/2011 |
| WO | 2011032040 A1 | 3/2011 |
| WO | WO 2011/032053 A1 | 3/2011 |
| WO | WO 2011/053987 A1 | 5/2011 |
| WO | WO 2011/151777 A1 | 12/2011 |
| WO | WO 2011/156529 A2 | 12/2011 |
| WO | WO 2012/013932 A1 | 2/2012 |
| WO | 2012/061832 A1 | 5/2012 |
| WO | 2012/054873 A3 | 8/2012 |
| WO | WO 2012/103154 A1 | 8/2012 |
| WO | WO 2013/059740 A1 | 4/2013 |
| WO | WO 2013/059746 A1 | 4/2013 |
| WO | WO 2013/112923 A1 | 8/2013 |
| WO | 2013/130512 A3 | 10/2013 |
| WO | WO 2013/177220 A1 | 11/2013 |
| WO | 2013/190441 A2 | 12/2013 |
| WO | WO 2013/191775 A2 | 12/2013 |
| WO | 2014/039556 A1 | 3/2014 |
| WO | 2014/082032 A1 | 5/2014 |
| WO | 2013/138510 A9 | 7/2014 |
| WO | WO 2014/144092 A1 | 9/2014 |
| WO | WO 2014/150931 A1 | 9/2014 |
| WO | 2015/031691 A1 | 3/2015 |
| WO | 2015/073711 A1 | 5/2015 |
| WO | 2015/104302 A1 | 7/2015 |
| WO | WO 2015/131107 A1 | 9/2015 |

OTHER PUBLICATIONS

Baldwin, A. et al., Multilocus sequence typing of Cronobacter sakazakii and Cronobacter malonaticus reveals stable clonal structures with clinical significance which do not correlate with biotypes, BMC Microbiology, vol. 9:223, pp. 1-9 (Year: 2009).*

BigDye Terminator v3.1 Cycle Sequencing Kit (Applied Biosystems, pp. 1-72 (Year: 2002).*

Shendure, J. et al., Accurate Multiplex Polony Sequencing of an Evolved Bacteria Genome, Science, vol. 309, Supplementary material, pp. 1-41 (Year: 2005).*

Voelkerding, K.B\V. et al., Next-Generation Sequencing: From Basic Research to Diagnostics, Clin. Chem., vol. 55, pp. 641-658 (Year: 2009).*

Smith, D.R. et al., Rapid whole-fenome mutational profiling using next-generation sequencing technologies, Genome Res., vol. 18, pp. 1638-1642 (Year: 2008).*

U.S. Appl. No. 13/980,987, filed Jul. 2, 2013, Kurn et al.
U.S. Appl. No. 14/778,564, filed Sep. 16, 2016, Amorese et al.
U.S. Appl. No. 14/836,936, filed Aug. 26, 2015, Amorese et al.
U.S. Appl. No. 14/877,075, filed Oct. 7, 2015, Kurn.
U.S. Appl. No. 14/920,254, filed Oct. 22, 2015, Armour.
U.S. Appl. No. 14/991,340, filed Jan. 8, 2016, Schroeder et al.
U.S. Appl. No. 14/995,882, filed Jan. 14, 2016, Armour.
AB Applied Biosystems. The solid 3 system enabling the next generation of science. Presentation. 2009.
Adamczyk, et al. Synthesis of a Chemiluminescent Acridinium Hydroxylamine (AHA) for the Direct Detection of Abasic Sites in DNA. Org. Lett. 1999; 1(5):779-781.
Adamczyk, et al. O-(Fluoresceinylmethyl) hydroxylamine (OFMHA): A Fluorescent Regent for Detection of Damaged Nucleic Acids. Bioorg. & Med. Chem. Lett. 1998; 8:3599-3602.
Adessi, et al., Solid phase DNA amplification: characterisation of primer attachment and amplfication mechanisms. Nucleic Acids Research. Oct. 15, 2000 28:(20): e87.
Agilent Technologies. Agilent Technologies adds human exon kit to next-generation-sequencing target enrichment portfolio. GenomicsNews.com. Posted 2009 Sep. 23, 2009. Avaialble at http://www.genomicsnews.com/index.aspx?ID=103607&sm=Agilent%20technologies%20adds%20human%20exo. Accessed Oct. 6, 2009.
Ahmed. Sequencing of Low-Diversity Libraries. Feb. 28, 2012. http://cofactorgenomics.com/sequencing-low-diversity-libraries/.
Albert, et al. Direct selection of human genomic loci by microarray hybridization. Nat Methods. Nov. 2007;4(11):903-5. Epub Oct. 14, 2007.
Alvarado, et al. Multiplexed direct genomic selection (MDiGS): a pooled BAC capture approach for highly accurate CNV and SNP/INDEL detection. Nucleic Acids Res. Jun. 2014;42(10):e82. doi: 10.1093/nar/gku218. Epub Mar. 20, 2014.
Anisimova, et al. Isolation, characterization and molecular cloning of duplex-specific nuclease from the hepatopancreas of the kamchatka crab. *BMC Biochemistry*. May 21, 2008. 9:14 doi10.1186/1471-2091-9-14.

(56) References Cited

OTHER PUBLICATIONS

Antson, et al. PCR-generated padlock probes detect single nucleotide variation in genomic DNA. Nucleic Acids Res. Jun. 15, 2000;28(12):E58.
Anwar, et al. A stem-loop-mediated reverse transcription real-time PCR for the selective detection and quantification of the replicative strand of an RNA virus. Anal Biochem. May 1, 2006;352(1):120-8. Epub Feb. 17, 2000.
Archer, et al. Selective and flexible depletion of problematic sequences from RNA-seq libraries at the cDNA stage. BMC Genomics. May 26, 2014;15:401. doi: 10.1186/1471-2164-15-401.
Arraystar, Inc. Arraystar Directional RNA-seq Prep Kit (dUTP Based). Cat#: A1208. Apr. 8, 2013.
Ausubel, et al., Eds. Current Protocols in Molecular Biology. John Wiley & Sons, Inc. 1987 and updates.
Baird, et al. Rapid SNP discovery and genetic mapping using sequenced RAD markers. PLoS One. 2008;3(10):e3376.
Ballestar, et al. Methyl-CpG-binding proteins. Targeting specific gene repression. Eur J Biochem 2001; 268:1-6.
Bangs Laboratories, Inc. TechNote 205 retreived at: http:www.bangslab.com/technotes/205.pdf . Visited on Jul. 16, 2003. (8 pages).
Bashiardes, et al. Direct genomic selection. Nat Methods. Jan. 2005;2(1):63-9.
Beaucage, et al. The functionalization of oligonucleotides via phosphoramidite derivative. Tetrahedron 1993;49(10):1925-63.
Beier, et al. HT sequencing in biomedicine—new approaches in preparing samples. *LABORWELT*. Jan. 9, 2008.
Ben-Artzi, et al. Double-stranded RNA-dependent RNase activity associated with human immunodeficiency virus type 1 reverse transcriptase. Proc Natl Acad Sci U S A. Feb. 1, 1992;89(3):927-31.
Bentley, D. R. Whole-genome re-sequencing. Curr Opin Genet Dev. Dec. 2006;16(6):545-52. Epub Oct. 18, 2006.
Bhattacharjee, et al. Complementing next generation sequencing technologies with Agilent's SureSelect DNA capture array. Agilent. Jul. 13, 2009.
Bibikova, et al. Targeted chromosomal cleavage and mutagenesis in drophila using zinc-finger nucleases genetics. *Genetics*. Jul. 2002. 161: 1169-1175.
Bioo Scientific. Illumina RNA-Seq Library Prep. Available at http://www.biooscientific.com/ProductsServices/NextGenSequencing/Illumina-Compatible/RNA-Seq.aspx. Accessed Jun. 16, 2014.
Bioo Scientific. NEXTflex RNA-Seq Kit. Available at http://www.biooscientific.com/ProductsServices/NextGenSequencing/Illumina-Compatible/RNA-Seq/NEXTflex%E2%84%A2RNA-SeqKit.aspx. Accessed Jun. 16, 2014.
Blow, N. Genomics: catch me if you can. *Nature Methods*.Jul. 2009. 6:7.539-544.
Bormann, et al. Whole methylome analysis by ultra-deep sequencing using two-base encoding. PLoS One. Feb. 22, 2010;5(2):e9320.
Borodina, et al. A strand-specific library preparation protocol for RNA sequencing. Methods Enzymol. 2011;500:79-98. doi: 10.1016/B978-0-12-385118-5.00005-0.
Boturyn, et al. A simple and Sensitive Method for in Vitro Quantitation of Abasic Sites in DNA. Chem. Res. Toxicol. 1999; 12:476-482.
Boturyn, et al. Synthesis of Fluorescent Probes for the Detection of Abasic Sites in DNA. Tetrahedron. 1997; 53(15):5485-5492.
Bower, et al. Targeted rapid amplification of cDNA ends (T-RACE)—an improved RACE reaction through degradation of non-target sequences. Nucleic Acids Res. Nov. 2010;38(21):e194. doi: 10.1093/nar/gkq816. Epub Sep. 15, 2010.
Briggs, et al. Targeted retrieval and analysis of five Neandertal mtDNA genomes. Science. Jul. 17, 2009;325(5938):318-21. doi: 10.1126/science.1174462.
Brill, et al. Synthesis of oligodeoxynucleoside phosphorodithioates via thioamidites. J. Am. Chem. Soc. 1989;111:2321-2322.
Broude. Stem-loop oligonucleotides: a robust tool for molecular biology and biotechnology. Trends Biotechnol. Jun. 2002;20(6):249-56.
Brown, T.A. Ed. Molecular Biology, LabFax. Bios Scientific Publishers. Academic Press. 1991; pp. 147-148.
Buchman, et al. Selective RNA amplification: a novel method using dUMP-containing primers and uracil DNA glycosylase. PCR Methods Appl. Aug. 1993;3(1):28-31.
Burrows, et al. Oxidative Nucleobase Modifications Leading to Strand Scission. Chem Rev. May 7, 1998;98(3):1109-1151.
Carey, et al. Human Apurinic/Apyrimidinic Endonuclease in Processive. Biochem. 1999; 38:16553-16560.
Carlsson, et al. Screening for genetic mutations. Nature. 1996;380(6570):207.
Chan, et al. The biophysics of DNA hybridization with immobilized oligonucleotide probes. Biophys J. Dec. 1995;69(6):2243-55.
Chen, et al. BisQC: an operational pipeline for multiplexed bisulfite sequencing. BMC Genomics. Apr. 16, 2014;15:290. doi: 10.1186/1471-2164-15-290.
Chen, et al. Real-time quantification of microRNAs by stem-loop RR-PCR. Nucleic Acids Res. Nov. 27, 2005;33(20):e179.
Chenchik, et al. Full-length cDNA cloning and determination of mRNA 5' and 3' ends by amplification of adaptor-ligated cDNA. Biotechniques. Sep. 1996;21(3):526-34.
Clontech Laboratories, Inc. In-Fusion SMARTer Directional cDNA Library Construction Kit User Manual. Cat. No. 634933. Copyright 2013.
CNV detection by ion semiconductor sequencing. Life Technologies. 2014.
COFACTOR genomics. Directional RNA Sequencing. Abailable at http://cofactorgenomics.com/directional-rna-sequencing. Accessed Jun. 4, 2014.
Combined search and examination report dated Apr. 24, 2013 for GB1305340.
Craig, et al. Identification of genetic variants using bar-coded multiplexed sequencing. Nat Methods. Oct. 2008;5(10):887-93.
Croucher, et al. A simple method for directional transcriptome sequencing using Illumina technology. Nucleic Acids Res. Dec. 2009;37(22):e148.
Dahl, et al. Multigene amplification and massively parallel sequencing for cancer mutation discovery. Proc Natl Acad Sci U S A. May 29, 2007;104(22):9387-92. Epub May 17, 2007.
Dahl, et al. Multiplex amplification enabled by selective circularization of large sets of genomic DNA fragments. Nucleic Acids Res. Apr. 28, 2005;33(8):e71.
Dempcy, et al. Synthesis of a thymidyl pentamer of deoxyribonucleic guanidine and binding studies with DNA homopolynucleotides. Proc Natl Acad Sci USA. 1995;92(13):6097-101.
Derisi, et al. Use of cDNA microarray to analyse gene expression patterns in human cancer. Nature Genetics. 1996; 14:457-460.
Diagnosing problems with phasing and pre-phasing on Illumina platforms. Loman Labs. Nov. 21, 2013. http://nickloman.github.io/high-throughput%20sequencing/2013/11/21/diagnosing-problems-with-phasing-and-pre-phasing-on-illumina-platforms/.
Dressman, et al., Transforming single DNA molecules into fluorescent magnetic particles for detection and enumeration of genetic variations. Proc Natl Sci USA. Jul. 22, 2003. 100(15): 8817-8822.
Drmanac, et al. Human genome sequencing using unchained base reads on self-assembling Dna nanoarrays. Science. Jan. 1, 2010;327(5961):78-81. doi: 10.1126/science.1181498. Epub Nov. 5, 2009.
Egholm, et al. Peptide nucleic acids (PNA) oligonucleotide analogues with an achiral peptide backbone. J. Am. Chem. Soc. 1992;114:1895-1897.
Egholm, et al. PNA hybridizes to complementary oligonucleotides obeying the Watson-Crick hydrogen-bonding rules. Nature. 1993;365(6446):566-8.
Erlanger, et al. Antibodies Specific for Ribonucleosides and Ribonucleotides and Their Reaction With DNA. Proc Natl Acad Sci USA. 1964; 52:68-74.
Esteller. Cancer epigenomics: DNA methylomes and histone-modification maps. Nat Rev Genet. Apr. 2007;8(4):286-98. Epub Mar. 6, 2007.
European office action dated Apr. 1, 2011 for Application No. 03771533.1.

(56) References Cited

OTHER PUBLICATIONS

European search report and opinion dated May 22, 2015 for EP Application No. 12842163.3.
European search report and opinion dated Nov. 28, 2013 for EP Application No. 11793123.8.
European search report and search opinion dated Apr. 3, 2013 for Application No. 10808789.1.
European search report dated Oct. 18, 2007 for Application No. 3771533.1.
European search report dated Feb. 12, 2010 for Application No. 7810169.8.
European search report dated Mar. 29, 2010 for Application No. 4815722.6.
Fadrosh, et al. An improved dual-indexing approach for multiplexed 16S rRNA gene sequencing on the Illumina MiSeq platform. Microbiome. Feb. 24, 2014;2(1):6. doi: 10.1186/2049-2618-2-6.
Fahy, et al., Self-sustained sequence replication (3SR): an isothermal transcription-based amplication system alternative to PCR. Genome Res. 1991. 1:25-33.
Faircloth, et al. Not all sequence tags are created equal: designing and validating sequence identification tags robust to indels. PLoS One. 2012;7(8):e42543. doi: 10.1371/journal.pone.0042543. Epub Aug. 10, 2012.
Feinberg, et al. Hypomethylation distinguishes genes of some human cancers from their normal counterparts. Nature. Jan. 6, 1983;301(5895):89-92.
Fodor, et al. Light-Directed, spatially addressable parallel chemical synthesis. 1991; 251: 767-773.
Franca, et al. Optimizing a qPCR gene expression quantification assay for S. epidermidis biofilms: a comparison between commercial kits and a customized protocol. PLoS One. 2012;7(5):e37480. doi: 10.1371/journal.pone.0037480. Epub May 21, 2012.
Frank. Barcrawl and Bartab: software tools for the design and implementation of barcoded primers for highly multiplexed DNA sequencing. BMC Bioinformatics. Oct. 29, 2009;10:362.
Fredriksson, et al. Multiplex amplification of all coding sequences within 10 cancer genes by Gene-Collector. Nucleic Acids Res. 2007;35(7):e47. Epub Feb. 22, 2007.
Freeman, et al. Fundamentals of DNA Hybridization Arrays for Gene Expression Analysis. BioTechniques. Nov. 2000; 29:1042-1044, 1046, 1048-1055.
Freshney, R.I. ed. (1987). *Animal Cell Culture*. IRL Press: Oxford, pp. vii-xii (Table of Contents Only.).
Fujiwara, et al. Direct probing: covalent attachment of probe DNA to double-stranded target DNA. Nucleic Acids Res. Dec. 15, 1998;26(24):5728-33.
Fullwood, et al. Next-generation DNA sequencing of paired-end tags (PET) for transcriptome and genome analyses. *Genome Research Open Access*. 2009. Available at http://genome.cshlp.org/content/19/4/521.long. Accessed Oct. 6, 2009.
Gait, M.J., Ed. 1984 . Oligonucleotide Synthesis: A Practical Approach. IRL Press: Oxford, pp. vii-xii (Table of Contents).
Gertz, et al. Transposase mediated construction of RNA-seq libraries. Genome Res. Jan. 2012;22(1):134-41. doi: 10.1101/gr.127373.111. Epub Nov. 29, 2011.
Ghosh, S.S. Synthesis of 5'-Oligonucleotide Hydrazide Derivatives and Their Use in Preparation of Enzyme-Nucleic Acid Hybridization Probes. Anal. Biochem. 1989; 178:43-51.
Gnirke, et al. Solution hybrid selection with ultra-long oligonucleotides for massively parallel targeted sequencing. Nature Biotechnology. Feb. 2009; 27(2):182-9.
Gu, et al. Partitioning the c. elegans genome by nucleosome modification, occupancy, and position. Online Aug. 25, 2009. http://www.springerlink.com/content/r0gw044155823242/fulltext.pdf. Accessed Oct. 6, 2009.
Gu, et al. Preparation of reduced representation bisulfite sequencing libraries for genome-scale DNA methylation profiling. Nat Protoc. Apr. 2011;6(4):468-81. doi: 10.1038/nprot.2010.190. Epub Mar. 18, 2011.

Haraguchi, et al. Synthesis and characterization of oligodeoxynucleotides containing formamidopyrimidine lesions and nonhydrolyzable analogues. J Am Chem Soc. Apr. 3, 2002;124(13):3263-9.
Heimgartner, et al.Polyacrylic Polyhydrazides as Reagents for Detection of Glycoproteins. Anal. Biochem. 1989; 181:182-189.
Hodges, et al. Genome-wide in situ exon capture for selective resequencing. Nat Genet. Dec. 2007;39(12):1522-7. Epub Nov. 4, 2007.
Hodges, et al. Hybrid selection of discrete genomic intervals on custom-designed microarrays for massively parallel sequencing. *Nat. Protoc.* 2009; 4(6): 960-974.
Hollis, et al. Structural studies of human alkyladenine glycosylase and *E. coli* 3-methyladenine glycosylase.Mutat Res. 2000; 460(3-4):201-10.
Horn, et al. Solid supported hydrolysis of apurinic sites in synthetic oligonucleotides for rapid and efficient purification on reverse-phase cartridges. Nucl. Acids Res. 1988; 16:11559-11571.
Hottiger, et al. Strand displacement activity of the human immunodeficiency virus type 1 reverse transcriptase heterodimer and its individual subunits. J Biol Chem. Jan. 14, 1994;269(2):986-91.
Huber, et al. Processing of the primer for plus strand DNA synthesis by human immunodeficiency virus 1 reverse transcriptase. J Biol Chem. Jun. 25, 1990;265(18):10565-73.
Ide, et al. Synthesis and Damage Specificity of a Novel Probe for the Detection of Abasic Sites in DNA. Biochem. 1993; 32:8276-8283.
Illumina Inc. Directional mRNA-Seq Sample Preparation—Application to prepare directional (strand specific) sample from mRNA. Oct. 2010.
International Preliminary Examination Report dated Mar. 22, 2006 for PCT Patent Application No. PCT/US03/15825 filed May 19, 2003, 9pages.
International search report and written opinion dated Jan. 27, 2012 for PCT Application. No. US2011/039683.
International search report and written opinion dated Feb. 12, 2013 for PCT/US2012/061218.
International search report and written opinion dated Feb. 24, 2011 for PCT Application. No. US10/55137.
International search report and written opinion dated Apr. 16, 2013 for PCT Application. No. US2013/023278.
International search report and written opinion dated May 10, 2012 for PCT Application. No. US2012/22448.
International search report and written opinion dated Jun. 18, 2015 for PCT/US2014/018112.
International search report and written opinion dated Jul. 15, 2014 for PCT Application. No. US2014/028356.
International search report and written opinion dated Jul. 29, 2014 for PCT Application. No. US2014/24581.
International search report and written opinion dated Oct. 18, 2013 for PCT Application. No. US2013/032606.
International search report and written opinion dated Dec. 3, 2010 for PCT Application. No. US10-45384.
International search report dated Jan. 2, 2008 for PCT Application No. US2007/15409.
International search report dated Jun. 14, 2005 for PCT Application No. US 2003/015825.
International search report dated Jul. 9, 2008 for PCT Application No. US2004/043710.
Jenkins, et al. The biosynthesis of carbocyclic nucleosides. Chem. Soc. Rev. 1995;169-176.
Jones, et al. The epigenomics of cancer. Cell. Feb. 23, 2007;128(4):683-92.
Kaboev, et al. PCR hot start using primers with the structure of molecular beacons (hairpin-like structure). Nucleic Acids Res. Nov. 1, 2000;28(21):E94.
Karata, et al. Construction of a circular single-stranded DNA template containing a defined lesion. DNA Repair (Amst). Jul. 4, 2009;8(7):852-6.
Karow. New Capture Method Enables MPI Team to Sequence Five Neandertal Mitochondrial Genomes. GenomeWeb. Jul. 21, 2009. https://www.genomeweb.com/sequencing/new-capture-method-enables-mpi-team-sequence-five-neandertal-mitochondrial-genom.

(56) References Cited

OTHER PUBLICATIONS

Kawarada, et al. Antibodies Specific for Methylated DNA Elicited in Rabbits Recognize only a Single Strand Region of DNA Containing 7-Methylguanine. Tohuku. J Exp Med. 1986; 149:151-161.
Khrapko, et al. A method for DNA sequencing by hybridization with oligonucleotide matrix. DNA Sequence—J. DNA Sequencing and Mapping. 1991; 1:375-388.
Kiedrowski, et al. Parabolic growth of a self-replicating hexadeoxynucleotide bearing a 3'-5'-phosphoamidate linkage. Angew. Chem. Intl. Ed. English 1991;30:423-426.
Kim, et al. Evidence for thiol-dependent production of oxygen radicals by 4-methyl-5-pyrazinyl-3H-1,2-dithiole-3-thione (oltipraz) and 3H-1,2-dithiole-3-thione: possible relevance to the anticarcinogenic properties of 1,2-dithiole-3-thiones. Chem Res Toxicol. Mar. 1997;10(3):296-301.
Koshkin, et al. LNA (Locked Nucleic Acid): An RNA mimic forming exceedingly stable LNA:LNA duplexes. J. Am. Chem. Soc. 1998; 120:13252-3.
Kow, et al. Detection of Abasic Sites and Oxidative DNA Base Damage Using an Elisa-like Assay. Methods. 2000; 22:164-169.
Kozich, et al. Development of a dual-index sequencing strategy and curation pipeline for analyzing amplicon sequence data on the MiSeq Illumina sequencing platform. Appl Environ Microbiol. Sep. 2013;79(17):5112-20. doi: 10.1128/AEM.01043-13. Epub Jun. 21, 2013.
Krishnakumar, et al. A comprehensive assay for targeted multiplex amplification of human DNA sequences. Proc Natl Acad Sci U S A. Jul. 8, 2008;105(27):9296-301. doi: 10.1073/pnas.0803240105. Epub Jul. 2, 2008.
Krueger, et al. Bismark: a flexible aligner and methylation caller for Bisulfite-Seq applications. Bioinformatics. Jun. 1, 2011;27(11):1571-2. doi: 10.1093/bioinformatics/btr167. Epub Apr. 14, 2011.
Krueger, et al. Large scale loss of data in low-diversity illumina sequencing libraries can be recovered by deferred cluster calling. PLoS One. Jan. 28, 2011;6(1):e16607. doi: 10.1371/journal.pone.0016607.
Krueger. Loss of data in low-diversity libraries can be recovered by deferred cluster calling. Poster Jan. 29, 2011. http://seqanswers.com/forums/showthread.php?t=9150.
Kubo, et al. A Novel Sensitive, and Specific Assay for Abasic Sites, the Most Commonly Produced DNA Lesion. Biochem. 1992; 31:3703-3708.
Kumar, et al. A High-Throughput Method for Illumina RNA-Seq Library Preparation. Front Plant Sci. Aug. 28, 2012;3:202. doi: 10.3389/fpls.2012.00202. eCollection 2012.
Kurn. Method for generation of double stranded cDNA from RNA targets useful for global amplification, sequencing or other quantification of short RNA in a sample. Mar. 21, 2010.
Laird. Principles and challenges of genomewide DNA methylation analysis. Nat Rev Genet. Mar. 2010;11(3):191-203. doi: 10.1038/nrg2732.
Lao, et al. Real time PCR profiling of 330 human micro-RNAs. Biotechnol J. Jan. 2007;2(1):33-5.
LC Sciences. Targeted sequencing—sample enrichment service. 2009. Available at www.lcsciences.com/products/genomics/targeted_sequencing/targeted_sequencing.html. Accessed Oct. 6, 2009.
LC Sciences. Technology—Massively parallel oligonucleotide and peptide synthesis on a micrchip based on the uParaflo microfluidic technology. Available at www.lcsciences.com/support/technology/technology.html. Accessed Oct. 6, 2009.
LC Sciences. Oligonucleotide mixture. OligoMix. 2009. Available at www.lcsciences.com/products/genomics/oligomix/oligomix_detail.html. Accessed Oct. 6, 2009.
Leamon, et al., a Massively parallel Pico TiterPlate based platform for discrete picoliter-scale polymerase chaine reactions [abstract]. *Electrophoresis*. Nov. 24, 2003(21) 3769-77.
Lefrancois, et al. Efficient yeast ChIP-Seq using multiplex short-read DNA sequencing. BMC Genomics. Jan. 21, 2009;10:37.

Lennon, et al. A scalable, fully automated process for construction of sequence-ready barcoded libraries for 454. Genome Biol. 2010;11(2):R15.
Leonard. What is a reliable method for multiplexing more than 384 samples on a MiSeq run? Posted Aug. 19, 2013. http://www.researchgate.net/post/What_is_a_reliable_method_for_multiplexing_more_than_384_samples_on_a_MiSeq_run2.
Letsinger, et al. Cationic oligonucletides. J. Am Chem. Soc. 1988; 110:4470-4471.
Letsinger, et al. Effects of pendant groups at phosphorus on binding properties of d-ApA analogues. Nucleic Acids Res. 1986;14(8):3487-99.
Letsinger, et al. Phosphoramidate analogs of oligonucleotides. J Org Chem. 1970;35(11):3800-3.
Levin, et al. Comprehensive comparative analysis of strand-specific RNA sequencing methods. Nat Methods. Sep. 2010;7(9):709-15. doi: 10.1038/nmeth.1491. Epub Aug. 15, 2010.
Lhomme, et al. Abasic DNA Structure reactivity and recognition. Biopolymers. 1999; 52(2): 65-83.
Lindahl, T. An N-Glycosidase from *Escherichia coli* That Releases Free Uracil from DNA Containing Deaminated Cytosine Residues. Proc Natl. Acad. Sci. USA 1974; 71(9):3649-3653.
Lizardi, et al., Mutation detection and single-molecule counting using isothermal rolling-circle amplification. *Nature Genetics*. 1998 Jul. 1998.19:(3):225-32.
Lockhart, et al. Expression monitoring by hybridization to high-density oligonucleotide arrays. Nature Biotechnology. 1996; 14:1675-1680.
Mag, et al. Synthesis and selective cleavage of an oligodeoxynucleotide containing a bridged internucleotide 5'-phosphorothioate linkage. Nucleic Acids Res. 1991;19(7):1437-41.
Makrigiogos, G. Fluorescent Labeling of Abasic Sites: A Novel Methodology to Detect Closey-Spaced Damage Sites in DNA. Int. J. Radiat. Biol. 1998: 74(1):99-109.
Marchuk, et al. Construction of T-vectors, a rapid and general system for direct cloning of unmodified PCR products. Nucleic Acids Res. Mar. 11, 1991; 19(5): 1154.
Mardis, E. New strategies and emerging technologies for massively parallel sequencing: applications in medical research. Online Apr. 17, 2009. *Genome Med*. 2009: 1(4); 40. Available at www.ncbinlm.nih.gov/pmc/aricles/PMC2684661/?tool=pubmed. Accessed Oct. 22, 2009.
Mardis. Next-Generation DNA Sequencing Methods. The Annual Review of Genomics and Human Genetics. 2008; 9:387-402.
Margulies, et al. Genome sequencing in microfabricated high-density picolitre reactors [abstract]. *Nature*. Sep. 15, 2005; 437 (7057): 376-80. Epub Jul. 31, 2005.
Maskos, et al. Oligonucleotide hybridisations on glass supports: a novel linker for oligonucleotide synthesis and hybridization properties of oligonucleotides synthesised in Situ. Nucl. Acids. Res. 20(7):1679-1684.
Maulik, et al. Novel Non-isotopic Detection of MutY Enzyme-recognized Mismatches in DNA Via Ultrasensitive Detection of Aldehydes. Nucl. Acids. Res. 1999: 27(5):1316-1322.
McCarthy, et al. Inducible repair of O-alkylated DNA pyrimidines in *Escherichia coli*. EMBO J. 1984; 3(3):545-50.
McClure, et al. Bovine exome sequence analysis and targeted SNP genotyping of recessive fertility defects BH1, HH2, and HH3 reveal a putative causative mutation in SMC2 for HH3. PLoS One. Mar. 25, 2014;9(3):e92769. doi: 10.1371/journal.pone.0092769. eCollection 2014.
McHugh, et al. Novel Regents for Chemical Cleavage at Abasic Sites and UV Photoproducts in DNA. Nucl. Acids. Res. 23(10): 1664-1670.
Meier, et al. Peptide nuclieic acids (PNAs)—Unusual properties of nonionic oligonucleotide analogues. Chem. Int. Ed. Engl. 1992;31:1008-1010.
Meissner, et al. Reduced representation bisulfite sequencing for comparative high-resolution DNA methylation analysis. Nucleic Acids Res. Oct. 13, 2005;33(18):5868-77. Print 2005.
Metzker, M. Sequencing technologies—the next generation. Nat Rev Genet. Jan. 2010;11(1):31-46. Epub Dec. 8, 2009.

(56) References Cited

OTHER PUBLICATIONS

Meuzelaar, et al. MegaPlex PCR: a strategy for multiplex amplification. Nat Methods. Oct. 2007;4(10):835-7. Epub Sep. 16, 2007.
Meyer, et al. Parallel tagged sequencing on the 454 platform. Nat Protoc. 2008;3(2):267-78. doi: 10.1038/nprot.2007.520.
Meyer, et al. Targeted high-throughput sequencing of tagged nucleic acid samples. Nucleic Acids Res. 2007;35(15):e97.
Mitchell, et al. Circulating microRNAS as stable blood-based markers for cancer detection. Proc Natl Acad Sci U S A. Jul. 29, 2008;105(30):10513-8. Epub Jul. 28, 2008.
Mitra, et al. Oxidative DNA cleavage by the antitumor antibiotic leinamycin and simple 1,2-dithiolan-3-one 1-oxides: Evidence for thiol-dependent conversion of molecular oxygen to DNA-cleaving oxygen radicals mediated by polysulfides. Journal of the American Chemical Society. 1997; vol. 119(48):11691-11692.
Mitra, et al., In situ localized amplification and contact replication of many individual DNA moecules. Nucleic Acids Research. 1999. 27:(24); e34.
Mizugaki, et al. Preparation of a monoclonal antibody specific for 5-methyl-2'deoxycytidine and its application for the detection of DNA methylation levels in human peripheral blood cells. Biol Pharm Bull. 1996; 19(12):1537-1540.
Molecular Probe Handbook Section 3.2 obtained from website at: http://www.probes.com/handbook/print/0302.html(Copyright© 1996-2003 by Molecular Probes, Inc.) Visited on Aug. 13, 2003. (18 pages).
Mullis, K.B et al., Eds. (1994). PCR: Polymerase Chain Reaction. Birkhauser: Boston, pp. xv-xvii (Table of Contents).
Myllykangas, et al. Efficient targeted resequencing of human germline and cancer genomes by oligonucleotide-selective sequencing. Nat Biotechnol. Oct. 23, 2011;29(11):1024-7. doi: 10.1038/nbt.1996.
Nakamura, et al. Highly Sensitive Apurinic/Apyrimidinic site Assay Can Detect Spontaneous and Chemically Induced Depurination Under Physiological Conditions. Cancer Res. 1998; 58:222-225.
Nayak, et al. Functional architecture of T7 RNA polymerase transcription complexes. *J. Mol Biol.* Aug. 10, 2007; 371(2): 490-500.
Nedderman, et al. Cloning and expression of human G/T mismatch-specific thymine-DNA glycosylase. J Biol Chem. 1996; 271(22):12767-74.
New England BioLabs Inc. NEBNext® Ultra™ Directional RNA Library Prep Kit for Illumina®. Available at https://www.neb.com/products/e7420-nebnext-ultra-directional-rna-library-prep-kit-for-illumina. Accessed Jun. 4, 2014.
Nextera® Rapid Capture Enrichment Low-Plex Pooling Guidelines. Technical Note: DNA Analysis. 2014. http://www.illumina.com/content/dam/illumina-marketing/documents/products/technotes/technote-nextera-rapid-capture-low-plex-pooling-guidelines.pdf.
Neylon, et al. Chemical and biochemical strategies for the randomization of protein encoding DNA sequences: library construction methods for directed evolution. Nucleic Acids Res. Feb. 27, 2004;32(4):1448-59. Print 2004.
Ng, et al. Targeted capture and massively parallel sequencing of 12 human exomes. *Nature*. Sep. 10, 2009. 461, 272-276. http://www.nature.com/nature/journal/v461/n7261/full/nature08250.html. Accessed Oct. 6, 2009.
Nikolaev, et al. Detection of genomic variation by selection of a 9Mb DNA region and high throughput sequencing. *PLoS ONE*. Aug. 17, 2009. 4(8): e6659.
Nugen, Inc. Ovation Biotin RNA Amplification and Labeling System User Guite. Catalog #2300-12. Published 2004.
Nugen, Inc. Technical Report #1. The Ovation Biotin System Validation for Use with Affymetrix GeneChip Arrays. Published 2004.
O'Shannessy, et al. Immobilization of Glycoconjugates by Their Oligosaccharides: Use of Hydrazido-Derivatized Matrices. Anal. Biochem. 1990; 191:1-8.
Ochman, et al. Genetic applications of an inverse polymerase chain reaction. Genetics. Nov. 1998;120(3):621-3.
Office action dated Jan. 16, 2013 for U.S. Appl. No. 12/938,112.
Office action dated Feb. 5, 2014 for U.S. Appl. No. 13/750,768.
Office action dated Feb. 8, 2012 for EP Application No. 07810169.8.
Office action dated Feb. 17, 2011 for U.S. Appl. No. 12/305,633.
Office action dated Feb. 28, 2013 for U.S. Appl. No. 13/156,294.
Office action dated Mar. 1, 2010 for U.S. Appl. No. 10/441,663.
Office action dated Mar. 7, 2007 for U.S. Appl. No. 10/441,663.
Office action dated Mar. 9, 2015 for CN Application No. 201380006942.4.
Office action dated Apr. 3, 2015 for CN Application No. 2012800608251.
Office action dated Apr. 16, 2014 for U.S. Appl. No. 13/239,226.
Office action dated May 16, 2011 for U.S. Appl. No. 11/948,784.
Office action dated May 25, 2006 for U.S. Appl. No. 10/441,663.
Office action dated Jun. 6, 2012 for U.S. Appl. No. 10/441,663.
Office action dated Jun. 19, 2013 for U.S. Appl. No. 12/855,611.
Office action dated Jun. 27, 2013 for U.S. Appl. No. 12/938,112.
Office action dated Jun. 30, 2008 for U.S. Appl. No. 11/026,280.
Office action dated Jul. 5, 2007 for U.S. Appl. No. 10/441,663.
Office action dated Jul. 8, 2009 for U.S. Appl. No. 10/441,663.
Office action dated Jul. 9, 2015 for U.S. Appl. No. 14/211,261.
Office action dated Jul. 13, 2007 for U.S. Appl. No. 11/026,280.
Office action dated Jul. 15, 2008 for U.S. Appl. No. 10/441,663.
Office action dated Jul. 15, 2015 for U.S. Appl. No. 13/750,768.
Office action dated Jul. 15, 2015 for U.S. Appl. No. 13/938,059.
Office action dated Aug. 18, 2010 for U.S. Appl. No. 12/305,633.
Office action dated Sep. 5, 2013 for U.S. Appl. No. 13/156,294.
Office action dated Sep. 9, 2010 for U.S. Appl. No. 10/441,663.
Office action dated Sep. 18, 2006 for U.S. Appl. No. 10/441,663.
Office action dated Sep. 24, 2009 for U.S. Appl. No. 10/441,663.
Office action dated Sep. 24, 2014 for U.S. Appl. No. 13/239,226.
Office action dated Sep. 25, 2014 for U.S. Appl. No. 13/750,768.
Office action dated Oct. 9, 2013 for U.S. Appl. No. 12/938,112.
Office action dated Oct. 14, 2010 for U.S. Appl. No. 11/948,784.
Office action dated Nov. 7, 2012 for U.S. Appl. No. 13/411,170.
Office action dated Nov. 13, 2012 for U.S. Appl. No. 12/855,611.
Office action dated Dec. 5, 2008 for U.S. Appl. No. 10/441,663.
Office action dated Dec. 17, 2007 for U.S. Appl. No. 10/441,663.
Okou, et al. Microarray-based genomic selection for high-throughput resequencing. Nat Methods. Nov. 2007;4(11):907-9. Epub Oct. 14, 2007.
Olson, M. Enrichment of super-sized resequencing targets from the human genome. Nat Methods. Nov. 2007;4(11):891-2.
Openwetware. Directional-RNAseq Prep. Available at http://openwetware.org/wiki/Directional-RNAseq_Prep. Accessed Jun. 4, 2014.
Pabinger, et al. A survey of tools for variant analysis of next-generation genome sequencing data. Brief Bioinform. Mar. 2014;15(2):256-78. doi: 10.1093/bib/bbs086. Epub Jan. 21, 2013.
Pang, et al. Use of modified nucleotides and uracil-DNA glycosylase (UNG) for the control of contamination in the PCR-based amplification of RNA. Molecular and Cellular Probes. 1992; 6:251-256.
Parameswaran, et al. A pyrosequencing-tailored nucleotide barcode design unveils opportunities for large-scale sample multiplexing. Nucleic Acids Res. 2007;35(19):e130.
Parkhomchuk, et al. Transcriptome analysis by strand-specific sequencing of complementary DNA. Nucleic Acids Res. Oct. 2009;37(18):e123.
Pauwels, et al. Biological activity of new 2-5A analogues. Chemica Scripta. 1986;26:141-9.
Pease, et al. A rapid, directional RNA-seq library preparation workflow for Illumina [reg] sequencing. Nature Methods. 2012; 9, No. 3.
Pease, et al. Light-generated oligonucleotide arrays for rapid DNA sequence analysis. Proc. Natl. Acad. Sci. USA 1994; 91:5022-5026.
Pease, et al. Rapid, directional RNA-seq library preparation kits for formalin-fixed paraffin-embedded RNA. Nature Methods. 2012; 9: Published online Sep. 27, 2012.
Pei, et al. Site-specific cleavage of duplex DNA by semisynthetic nuclease via triple-helix formation. *Pro. Natl. Acad. Sci. USA.* Dec. 1990. 87: 9858-9862.
Peng, et al. Kamchatka crab duplex-specific nuclease-mediated transcriptome subtraction method for identifying long cDNAs of differentially expressed genes. *Analytical Biochemistry.* Jan. 15, 2008. 372:2, 148-155. (abstract).

(56) References Cited

OTHER PUBLICATIONS

Pierce, et al. Linear-after-the-exponential polymerase chain reaction and allied technologies. Real-time detection strategies for rapid, reliable diagnosis from single cells. Methods Mol Med. 2007;132:65-85.
Pollack, et al. Genome-wide analysis of DNA copy-number changes using cDNA microarrays. Nature Genet. 1999; 23:41-46.
Porreca, et al. Multiplex amplification of large sets of human exons. Nat Methods. Nov. 2007;4(11):931-6. Epub Oct. 14, 2007.
Prashar, et al. Analysis of differential gene expression by display of 3' end restriction fragments of cDNAs. Proc Natl Acad Sci U S A. Jan. 23, 1996;93(2):659-63.
Proudnikov, et al. Chemical methods of DNA and RNA fluorescent labeling. Nucleic Acids Res. Nov. 15, 1996;24(22):4535-42.
Ramsahoye, et al. Non-CpG methylation is prevalent in embryonic stem cells and may be mediated by DNA methyltransferase 3a. Proc Nail Acad Sci U S A. May 9, 2000;97(10):5237-42.
Ranasinghe, et al. Fluorescence based strategies for genetic analysis. Chem Commun (Camb). Nov. 28, 2005;(44):5487-502. Epub Sep. 30, 2005.
Rawls, R. Optimistic about antisense. Promising clinical results and chemical strategies for further improvements delight antisense drug researchers. C & E News. Jun. 2, 1997; 35-59.
Riley, et al. A novel, rapid method for the isolation of terminal sequences from yeast artificial chromosome (YAC) clones. Nucleic Acids Res. May 25, 1990;18(10):2887-90.
Roberts, R. Restriction enzymes at NEB: over 30 years of innovation, the discovery, cloning and engineering of these essential reagents. *NEB Expression*. Winter. 2008. vol. 2.4. Available at www.neb.com/nebecomm/tech_reference/restriction_enzymes/feature_article_innovation.asp. Accessed Aug. 16, 2010.
Robertson. DNA methylation and human disease. Nat Rev Genet. Aug. 2005;6(8):597-610.
Roche Company. 454 life sciences, applications—sequence capture targeted region. http://www.454.com/applications/sequence-capture-targeted-region.asp. Accessed Oct. 6, 2009.
Saiki, et al. Analysis of enzymatically amplified beta-globin and HLA-DQ alpha DNA with allele-specific oligonucleotide probes. Nature. Nov. 13-19, 1986;324(6093):163-6.
Sambrook, J. et al., Eds. (1989). *Molecular Cloning: A Laboratory Manual*. 2nd Edition, Cold Spring Harbor Laboratory Press, pp. xi-xxxviii (Table of Contents).
Sanders, et al. Targeting individual subunits of the FokI restriction endonuclease to specific DNA strands, *Nucleic Acids Research*. Apr. 2009. *Nucleic Acids Res*. 37:(7):2105-15.
Sanghvi, et al. ed. Chapters 2 and 3, ASC Symposium Series 580—Carbohydrates Modifications in Antisense Research. American Chemical Society. Washington, DC. 1994.
Sanghvi, et al. ed. Chapters 6 and 7, ASC Symposium Series 580—Carbohydrates Modifications in Antisense Research. American Chemical Society. Washington, DC. 1994.
Sano, et al. Detection of heavy methylation in human repetitive DNA subsets by a monoclonal antibody against 5-methylcytosine. Biochim Biophys Acta. 1988; 951(1):157-65.
Sartori, et al. A novel uracil-DNA glycosylase with broad substrate specificity and an unusual active site. EMBO J. 2002; 21(12):3182-91.
Sawai, et al. Synthesis and properties of oligoadenylic acids containing 2'-5' phosphoramide linkage. Chem. Lett. 1984; 805-808.
Schena, et al. Parallel human genome analysis: microarray-based espression monitoring of 1000 genes. Proc Natl. Acad. Sci. USA Biochemistry. 1996; 93:10614-10619.
Schena, et al. Quantitative monitoring of gene expression patterns with a complementary DNA microarray. Science. 1995; 270:467-470.
Schmid, et al. Chic and chec: genomic mapping of chromatin proteins. *Molecular Cell*. 2004. 16, No. 1, pp. 147-157. (abstract).
SEQanswers. MiSeq cluster generation problems. Posted Mar. 17, 2012. http://seqanswers.com/forums/showthread.php?t=18499.
SEQanswers. Sequencing a Low diversity library on the HiSeq. Posted Nov. 18, 2011. http://seqanswers.com/forums/showthread.php?t=18499.
Shalon, et al. Parallel human genome analysis: microarray system for analyzing complex DNA samples using two-color fluorescent probe hybridization. Genome Res. 1996; 6:639-645.
Shendure, et al. Accurate multiplex polony sequencing of an evolved bacterial genome. Science. Sep. 9, 2005;309(5740):1728-32. Epub Aug. 4, 2005.
Shendure, et al. Accurate multiplex polony sequencing of an evolved bacterial genome. Science. Sep. 9, 2005;309(5741):1728-32. Epub Aug. 4, 2005. Supplemental Materials. 41 pages.
Shida, et al. Cleavage of Single-and double-Stranded DNAs Containing an Abasic Residue by *Escherichia coli* Exonuclease III (AP Endonuclease VI) Nucl. Acids. Res. 1996; 24(22):4572-4576.
Singapore exam report dated Apr. 7, 2015 for SG Application No. 11201404243W.
Singapore written opinion dated Mar. 17, 2015 for SG Application No. 11201401628W.
Slupphaug, et al. Low incorporation of dUMP by some thermostable DNA polymerases may limit their use in PCR amplifications. Anal. Biochem. 1993; 211:164-169.
Sohail, et al. Human activation-induced cytidine deaminase causes transcription-dependent, strand-biased C to U deaminations. Nucleic Acids Res. 2003; 31(12):2990-4.
Soni, et al. Progress toward ultrafast DNA sequencing using solid-state nanopores. Clin Chem. Nov. 2007;53(11):1996-2001. Epub Sep. 21, 2007.
Sprinzl, et al. Enzymatic incorporation of ATP and CTP analogues into the 3' end of tRNA. Eur J Biochem. Dec. 1997;81(3):579-89.
Srivastava, et al. Mammalian Abasic Site Base Excision Repair. Identification of the Reaction Sequence and Rate-Determining Steps. J. Biol. Chem. 1998; 273(33):21203-21209.
Stemimer, et al. Single-step assembly of a gene and entire plasmid from large numbers of oligodeoxyribonucleotides. Gene. Oct. 16, 1995;164(1):49-53.
Stephpens, et al. Automating sequence-based detection and genotyping of SNPs from diploid samples. Nat Genet. Mar. 2006;38(3):375-81. Epub Feb. 19, 2006.
Steullet, et al. Clevage of Abasic Sites in DNA by Intercalator-amines. Bioorganic and Medicinal Chem. 1999; 7:2531-2540.
Stratagene catalog, Gene Characterizatin Kits. 1988 p. 39.
Sugiyama, et al. Chemistry of thermal degradation of abasic sites in DNA. Mechanistic investigation on thermal DNA stand clevage of alkylated DNA. Chem. Res. Toxicol. 1994; 1:673-683.
Summerer, D. Enabling technologies of genomic-scale sequence enrichment for targeted high-throughput sequencing. *Genomics*. Dec. 2009;94(6):363-8. (abstract).
Sumimerer, et al. Microarray-based muticycle-enrichment of genomic subsets for targeted next-generation sequencing. Accepted Jun. 18, 2009. Available at www.ncbi.nlm.nih gov/pubmed/19638418. Accessed Oct. 6, 2009.
Timblin, et al. Application for PCR technology to subtractive cDNA cloning: identification of genes expressed specifically in murine plasmacytoma cells. Nucleic Acids Res. Mar. 25, 1990;18(6):1587-93.
Tong, et al. Detection of restriction enzyme-digested target DNA by PCR amplification using a stem-loop primer: application to the detection of hypomethylated fetal DNA in maternal plasma. Clin Chem. Nov. 2007;53(11):1906-14. Epub Sep. 27, 2007.
Turner, et al. Methods for genomic partitioning. Annu Rev Genomics Hum Genet. 2009;10:263-84. doi: 10.1146/annurev-genom-082908-150112.
Vairapandi, et al. Partial purification and characterization of human 5-methylcytosine-DNA glycosylase. Oncogene. 1996; 13(5):933-8.
Vairapandi, et al. Human DNA-demethylating activity: a glycosylase associated with RNA and PCNA. J Cell Biochem. 2000; 79(2):249-60.
Varkonyi-Gasic, et al. Protocol: a highly sensitive RT-PCR method for detection and quantification of microRNAs. Plant Methods. Oct. 12, 2007;3:12.

(56) References Cited

OTHER PUBLICATIONS

Varley, et al. Nested Patch PCR enables highly multiplexed mutation discovery in candidate genes. Genome Res. Nov. 2008;18(11):1844-50. doi: 10.1101/gr.078204.108. Epub Oct. 10, 2008.
Vincent, et al. Helicase-dependent isothermal DNA amplification. EMBO Rep. Aug. 2004;5(8):795-800. Epub Jul. 9, 2004.
Vos, et al. AFLP: a new technique for DNA fingerprinting. Nucleic Acids Res. Nov. 11, 1995;23(21):4407-14.
Walker, et al., Strand displacement amplification—an isothermal, in vitro DNA amplifcation technique. Nucleic Acids Resarch. 1991. 20(7): 1691-1696.
Westburg. Fast, Directional RNA-Seq Library Prep. Available at http://www.westburg.eu/lp/rna-seq-library-preparation. Accessed on Jun. 4, 2014.
Westin, et al., Anchored multiplex amplification on a microelectronic chip array. Nature Biotechnology. Feb. 18, 2000(2):199-204.
Wikipedia. ABI solid sequencing. Http://en.wikipedia.org/wiki/ABI_Solid_Sequencing. Last modified Oct. 4, 2009 Accessed Oct. 22, 2009.
Wikipedia. DNA sequencing. Available at http://en.wikipedia.org/wiki/Next-generation_sequencing. Last modified Oct. 8. 2009. Accessed Oct. 22, 2009.
Wilchek, et al. Labeling Glycoconjugates with Hydrazide Reagents. Methods Enzymol. 1987; 138:429-442.
Wolffe, et al. DNA demethylation. Proc Natl Acad Sci USA. 1999; 96(11):5894-6.
Wu, et al. Phasing Amplicon Sequencing for Robust Microbial Community Analysis. I-2630. 2014. http://www.asmonlineeducation.com/php/asm2014abstracts/data/papers/I-2630.htm.
Xiao, et al. Sequential amplification of flanking sequences by Y-shaped adaptor dependent extension using multiple templates. Zhi Wu Sheng Li Yu Fen Zi Sheng Wu Xue Xue Bao (Journal of Plant Physiology and Molecular Biology). Feb. 2007;33(1):85-90.
Young, et al. A new strategy for genome assembly using short sequence reads and reduced representation libraries. Genome Res. Feb. 2010;20(2):249-56. doi: 10.1101/gr.097956.109.
Zalipsky, S. Functionalized Poly(ethylene glycol) for Preparation of Biologically Relevant Congugates. Bioconjugate Chem. 1995; 6:150-165.
Zang, et al. DNA alkylation by leinamycin can be triggered by cyanide and phosphines. Bioorg Med Chem Lett. Jun. 18, 2001;11(12):1511-5.
Zhang, et al. Multiplex sequencing on the SOLID platform with 10, 16, or 96 barcodes. 2009 Life technologies. www3.appliedbiosystems.com/cms/groups/mcb_marketing/documents/generaldocuments/cms_065528.pdf.
Zheng, et al. Titration-free 454 sequencing using Y adapters. Nat Protoc. Aug. 18, 2011;6(9):1367-76. doi: 10.1038/nprot.2011.369.
Zhu, et al. Overexpression of 5-methylcytosine DNA glycosylase in human embryonic kidney cells EcR293 demethylates the promoter of a hormone-regulated reporter gene. Proc Natl Acad Sci USA. 2001; 98(9):5031-6.
Zhu, et al. 5-Methylcytosine DNA glycosylase activity is also present in the human MBD4 (G/T mismatch glycosylase) and in a related avian sequence. Nucleic Acids Res. 2000; 28(21):4157-65.
Zhulidov, et al. Simple cDNA normalization using kamchatka crab duplex=specific nuclease. *Nucleic Acids Research*. Online Feb. 18, 2004. 32:3 e37.
Ziller, et al. Genomic distribution and inter-sample variation of non-CpG methylation across human cell types. PLoS Genet. Dec. 2011;7(12):e1002389. doi:10.1371/journal.pgen.1002389. Epub Dec. 8, 2011.
Beaucage et al. Deoxynucleoside Phosphoramidites—A New Class of Key Intermediates for Deoxypolynucleotide Synthesis. Tetrahedron Letters. 1981;22(20):1859-1862.
Brown, et al. Chemical synthesis and cloning of a tyrosine tRNA gene. Methods Enzymol. 1979;68:109-51.
Callow, et al. Selective DNA amplification from complex genomes using universal double-sided adapters. Nucleic Acids Res. Jan. 28, 2004;32(2):e21.

European search report and opinion dated Jul. 23, 2015 for EP Application No. 13740653.
Froussard. A random-PCR method (rPCR) to construct whole cDNA library from low amounts of RNA. Nucleic Acids Res. Jun. 11, 1992;20(11):2900.
Ganova-Raeva, et al. Primer Extension Enrichment Reaction (PEER): a new subtraction method for identification of genetic differences between biological specimens. Nucleic Acids Research. 2006; 34(11):e76.
Gundmundsson, et al. Genome-wide association and replication studies identify four variants associated with prostate cancer susceptibility. Nat Genet. Oct. 2009;41(10):1122-6. doi: 10.1038/ng.448. Epub Sep. 20, 2009.
Narang, et al. Improved phosphotriester method for the synthesis of gene fragments. Methods Enzymol. 1979;68:90-8.
Notice of allowance dated Jul. 28, 2015 for U.S. Appl. No. 13/643,056.
Office action dated Oct. 30, 2015 for U.S. Appl. No. 13/750,768.
Office action dated Nov. 4, 2015 for U.S. Appl. No. 14/030,761.
Out, et al. Deep sequencing to reveal new variants in pooled DNA samples. Hum Mutat. Dec. 2009;30(12):1703-12. doi: 10.1002/humu.21122.
Tewhey, et al. Microdroplet-based PCR enrichment for large-scale targeted sequencing. Nat Biotechnol. Nov. 2009;27(11):1025-31. doi: 10.1038/nbt.1583. Epub Nov. 1, 2009.
Tucker, et al. Massively parallel sequencing: the next big thing in genetic medicine. Am J Hum Genet. Aug. 2009;85(2):142-54. doi: 10.1016/j.ajhg.2009.06.022.
Turner, et al. Massively parallel exon capture and library-free resequencing across 16 genomes. Nat Methods. May 2009;6(5):315-6. doi: 10.1038/nmeth.f.248. Epub Apr. 6, 2009.
Vater, et al. Short bioactive Spiegelmers to migraine-associated calcitonin gene-related peptide rapidly identified by a novel approach: tailored-SELEX. Nucleic Acids Res. Nov. 1, 2003;31(21):e130.
Voelkerding, et al. Next-generation sequencing: from basic research to diagnostics. Clin Chem. Apr. 2009;55(4):641-58. doi: 10.1373/clinchem.2008.112789. Epub Feb. 26, 2009.
Zhong, et al. High-throughput illumina strand-specific RNA sequencing library preparation. Cold Spring Harb. Protoc.; 2011; 940-949. doi:10.1101/pdb.prot5652.
Bodi, et al. Comparison of Commercially Available Target Enrichment Methods for Next-Generation Sequencing. J Biomol Tech. Jul. 2003; 24(2): 73-86.
European search report and opinion dated Jan. 29, 2016 for EP Application No. 13806978.
International search report and written opinion dated Feb. 5, 2016 for PCT/US2015/047053.
Ovation® Target Enrichment System. User guide. Nugen. 2016. 45 pages.
Watson, et al. Cloning and assembly of PCR products using modified primers and DNA repair enzymes. Biotechniques. Nov. 1997;23(5):858-62, 864.
U.S. Appl. No. 15/047,448, filed Feb. 18, 2016, Huelga et al.
Zhang, et al. Copy number variation in human health, disease, and evolution. Annu Rev Genomics Hum Genet. 2009;10:451-81. doi: 10.1146/annurev.genom.9.081307.164217.
Levesque-Sergerie, et al. Detection limits of several commercial reverse transcriptase enzymes: impact on the low- and high-abundance transcript levels assessed by quantitative RT-PCR. BMC Mol Biol. Oct. 22, 2007;8:93.
Office action dated Apr. 4, 2016 for U.S. Appl. No. 14/995,882.
Office action dated Apr. 7, 2016 for U.S. Appl. No. 14/390,012.
Gerrish, et al. Tailed pooled suppression subtractive hybridization (PSSH) adaptors do not alter efficiency. Antonie Van Leeuwenhoek. Nov. 2010;98(4):573-9. doi: 10.1007/s10482-010-9465-x. Epub Jun. 8, 2010.
Olivarius, et al. High-throughput verification of transcriptional starting sites by Deep-RACE. Biotechniques. Feb. 2009;46(2):130-2. doi: 10.2144/000113066.
U.S. Appl. No. 15/154,414, filed May 13, 2016, Armour et al.
Gu, et al. Depletion of Abundant Sequences by Hybridization (DASH): using Cas9 to remove unwanted high-abundance species in sequencing libraries and molecular counting applications. Genome Biology. 2016; 17:41. DOI: 10.1186/s13059-016-09045.

(56) References Cited

OTHER PUBLICATIONS

Oyola, et al. Efficient Depletion of Host DNA Contamination in Malaria Clinical Sequencing. J. Clin. Microbiol. Mar. 2013; 51(3):745-751.
Office action dated Jun. 2, 2016 for U.S. Appl. No. 13/750,768.
Rothberg, et al. An integrated semiconductor device enabling non-optical genome sequencing. Nature. Jul. 20, 2011;475(7356):348-52. doi: 10.1038/nature10242. With supplemental information.
Bradford, et al. A comparison of massively parallel nucleotide sequencing with oligonucleotide microarrays for global transcription profiling. BMC Genomics. May 5, 2010;11:282. doi: 10.1186/1471-2164-11-282.
Hurd, et al. Advantages of next-generation sequencing versus the microarray in epigenetic research. Brief Funct Genomic Proteomic. May 2009;8(3):174-83. doi: 10.1093/bfgp/elp013. Epub Jun. 17, 2009.
Office action dated Jul. 21, 2016 for U.S. Appl. No. 14/634,326.
European search report and opinion dated Sep. 1, 2016 for EP Application No. 14764629.3.
Office action dated Sep. 8, 2016 for U.S. Appl. No. 14/390,012.
Stewart, et al. Complete MHC Haplotype Sequencing for Common Disease Gene Mapping. Genome Res. Jun. 2004;14(6):1176-87. Epub May 12, 2004.
Office Action dated Oct. 31, 2016 for European Application 13806978.6.
Amos, 2000, DNA pooling in mutation detection with reference to sequence analysis, Am J Hum Genet 66:1689-1692.
Bellos, 2014, cnvCapSeq: detecting copy number variation in long-range targeted resequencing data, Nucleic Acids Res 42(20):e158.
Benson, 2013, Genbank, Nucl Acids Res 41:D36-D42.
Blomquist, 2013, Targeted RNA-Sequencing with Competitive Multiplex-PCR Amplicon Libraries, PLOS ONE 8(11): e79120.
Bodi, 2013, Comparison of commercially available target enrichment methods for next-generation sequencing, J Biomolecular Tech 24:73-86.
Browning, 2011, Haplotype phasing: existing methods and new developments, Nature Rev Gen, 12(10):703-714.
Church, 1988, Multiplexed DNA sequencing, Science 240:185-188.
Colbert, 2001, High-throughput screening for induced point mutations, Plant Physiol 126:480-484.
Collard, 2005, An introduction to markers, quantitative trait loci (QTL) mapping and marker-assisted selection for crop Improvements: the basic concepts Euphytica 142:169-196.
Eminaga, 2013, Quantification of microRNA Expression with Next-Generation Sequencing, Unit 4.17 in Current Protocols in Molecular Biology, Wiley, New York, NY (14 pages).
Fakhrai-Rad, 2002, Pyroseqeuncing: An accurate detection platform for single nucleotide polymorphisms, Human Mutation 19:479-485.
Frederico, 1990, A sensitive genetic assay for the detection of cytosine deamination: determination of rate constants and the activation energy, Biochemistry 29(10):2532-2537.
Genereux, 2008, Errors in the bisulfite conversion of DNA: modulating inappropriate and failed conversion frequencies, Nucl Acids Res 36(22):e150.
Grothues, 1993, PCR amplification of megabase DNA with tagged random primers (T-PCR), Nucl Acids Res 21:1321-1322.
Hajibabaei, 2005, Critical factors for assembling a high volume of DNA barcodes, Phil Trans R Soc B 360:1959-1967.
Illumina, 2011, TruSeq RNA and DNA Sample Preparation Kits v2, 1-15 Illumina, dated 27 Apr. 27, 2011 (4 pages).
International Search Report and Written Opinion dated Jan. 3, 2019, for PCT/US2018/056485, filed Oct. 18, 2018 (11 pages).
International Search Report and Written Opinion dated Jan. 6, 2016, for PCT/US15/44065, filed Aug. 6, 2015 (21 pages).
ntemational Search Report and Written Opinion dated Jul. 10, 2017, for Application No. PCT/US17/27060, filed Apr. 11, 2017 (9 pages).
International Search Report and Written Opinion dated Jun. 7, 2019, for PCT/US19/22527, filed Mar. 15, 2019 (15 pages).
International Search Report and Written Opinion dated Mar. 5, 2015, in international patent application PCT/US2014/065530, filed Nov. 13, 2014 (12 pages).
International Search Report and Written Opinion dated Dec. 14, 2018, for PCT/US2018/056717, filed Oct. 19, 2018.
Ion Total RNA-Seq Kit v2, User Guide, 2012, Life Technologies (82 pages).
Jiang, 2015, CODEX: a normalization and copy number variation detection method for whole exome sequencing, Nucleic Acids Res 43(6):e39.
Krumm, 2012, Copy number variation detection and genotyping from exome sequence data, Genome Res 22 (8):1525-1532.
Lai 2004, Characterization of the maize endosperm transcriptome and its comparison to the rice genome, Genome Res14:1932-1937.
Langmead, 2009, Ultrafast and memory-efficient alignment of short DNA sequences to the human genome, Genome Biol 10:R25.
Li, 2012, CONTRA: copy number analysis for targeted resequencing, Bioinformatics 28(10):1307-1313.
Lindstrom, 2004, Pyrosequencing for detection of Lamivudine-resistant Hepatitis B virus, J Clin Microb 42 (10):4788-4795.
Liu 2008, Sequence space coverage, entropy of genomes and the potential to detect non-human DNA in human samples, BMC Genomics 9(509):1-17.
Ma, 2015, Quantitative Analysis of Copy Number Variants Based on Real-Time LightCycler PCR, Curr Protoc Hum Genet 80:7.2.1.1-723.8.
Machine translation generated on Mar. 7, 2018, of CN 105890722 by website of European Patent Office (4 pages).
Margulies, 2005, Genorne sequencing in open microfabricated high density picoliter reactors, Nature 437 (7057):376-380.
Mauk, 2018, Simple Approaches to Minimally-Instrumented, Microfluidic-Based Point-of-Care Nucleic Acid Amplification Tests, Biosensors 8(1):e17.
McCloskey, 2007, Encoding PCR products with batch-stamps and barcodes, Biochem Genet 45:761-767.
Merriman, 2012, Progress in Ion Torrent semiconductor chip based sequencing, Electrophoresis, 35(23):3397-3417.
Miner, 2004, Molecular barcodes detect redundancy and contamination in hairpin-bisulfite PCR, Nucl Acids Res 32 (17):e135.
Myers, 2013, Protocol for Creating Multiplexed miRNA Libraries for Use in Illumina Sequencing, Myers lab microRNA-seq Protocol, Hudson Alpha Institute for Biotechnology web site, dated May 2, 2013, (15 pages).
NuGEN, 2014, User Guide Ovation Target Enrichment System, NuGEN Technologies Inc., San Carlos, CA (45 pages).
Nugen, 2016, Ovation RNA-Seq User Guide, NuGEN Technologies, Inc., San Carlos, CA (42 pages).
Plagnol, 2012, A robust model for read count data in exome sequencing experiments and implications for copy number variant calling, Bioinformatics 28(21):2747-2754.
Qiu, 2003, DNA sequence-based "bar-codes" for tracking the origins of expressed sequence tags from a maize cDNA library constructed using multiple mRNA sources, Plant Physiol 133:475-481.
Querfurth, 2012, Creation and application of immortalized bait libraries for targeted enrichment and next-generation sequencing, Biotechniques 52(6):375-380.
Ronaghi, 2001, Pyrosequencing sheds light on DNA sequencing, Genome Res 11:3-11.
Sathirapongsasuti, 2011, Exome sequencing-based copy-number variation and loss of heterozygosity detection: ExomeCNV, Bioinformatics 27(19):2648-2654.
Schiemer, 2011, Illumina TruSeq Adapters Demystified,Tufts University Core Facility XP055357867 (5 pages).
Shapero, 2001, SNP Genotyping by multiplexed solid-phase amplification and fluorescent minisequencing, Genome Res 11:1926-1934.
Shendure, 2005, Accurate multiplex polony sequencing of an evolved bacterial genome, Science 309:1728.
Soni, 2007, Progress toward ultrafast DNA sequencing using solid-state nanopores, Clin Chem 53(11):1996-2001.
Sood, 2006, Methods for reverse genetic screening in zebrafish by resequencing and TILLING, Methods 39:220-227.

(56) References Cited

OTHER PUBLICATIONS

Staroscik, 2004, Calculator for determining the number of a template, URI Genomics, webpage archive dated Apr. 6, 2017 (1 page), Retreived from the internet on Mar. 7, 2018, from <https://web.archive.org/web/20170406174850/http://cels.uri.edu/gsc/cndna.html>.

Steffens, 2017, A versatile and low-cost open source pipetting robot for automation of toxicological and ecotoxicological bioassays, PLoS One 12(6):e0179636.

Stratagene, 1998, Gene characterization kits, Stratagene Catalog, p. 39 (2 pages).

Supplementary European search report and opinion dated Jan. 30, 2018, for European patent application No. 15830393.3 (6 pages).

Till, 2003, Large-scale discovery of induced point mutations with high-throughput TILLING, Genome Res 13:524-530.

Trapnell, 2010, Transcript assembly and quantification by RNA-Seq reveals unannotated transcripts and isoform switching during cell differentiation, Nat Biotech 28:511-515.

Trapnell, 2013, Differential analysis of gene regulation at transcript resolution with RNA-seq, Nat Biotech 31:46-53.

Unemo, 2004, Molecular typing of Neisseria gonorrhoeae isolates by pyrosequencing of highly polymorphic segments of the porB gene, J Clin Microb 42(7):2926-2934.

Vigal, 2002, A review on SNP and other types of molecular markers and their use in animal genetics, Genet Sel Evol 34:275-305.

Walker, 1992, Strand displacement amplification—an isothermal, in vitro DNA amplification technique, Nucl Acids Res 20(7):1691-1696.

Westin 2000, Anchored multiplex amplification on a microelectronic chip array, Nat Biotech 18:199-204.

Wienholds, 2004, Target-selected gene inactivation in zebrafish, Meth Cell Biol 77:69-90.

Wolford, 2000, High-throughput SNP detection by using DNA pooling and denaturing high performance liquid chromatography (DHPLC), Hum Genet 107:483-487.

Xi, 2011, Copy number variation detection in whole-genome sequencing data using the Bayesian information criterion, PNAS 108(46):e1128-e1136.

Xu, 2012, FastUniq: A fast de novo duplicates removal tool for paired short reads, PLoSOne 7(12):e52249.

\* cited by examiner

SEQUENTIAL SEQUENCING

CROSS-REFERENCE

This application is a continuation of U.S. Ser. No. 14/211,261 filed Mar. 14, 2014, which claims the benefit of U.S. Provisional Application No. 61/801,600, filed Mar. 15, 2013, all of which are incorporated herein by reference in their entirety.

BACKGROUND OF THE INVENTION

Short read next generation sequencing (NGS) analysis has some limitations in both research and diagnostics. One key drawback is the problem of phasing. That is, when interrogating multiple loci of sequence variation, it is often impossible to determine which loci are co-located on the same chromosome or on the same chromosomal fragment. One example of a phasing problem occurs in diploid organisms in which two parental chromosomes, one from the mother and one from the father, are inherited, resulting in two copies of each gene (except for the genes carried on the sex chromosomes). Within each copy of the two copies of a gene in a diploid cell are regions of sequence variation, or loci, that fall within distinct sequence types known as alleles. Thus, allelic variation across different loci might exist within a single chromosome (maternal or paternal) of a chromosome pair, or across both chromosomes of a chromosome pair. Determining which loci or regions of sequence variation are co-located on the same (maternal or paternal) chromosome is useful for a variety of reasons, as discussed further below.

The pattern of alleles within each individual chromosome is referred to as haplotype. Haplotyping has many diagnostic and clinical applications. For example, two inactivating mutations across different loci within a single gene might be of little or no consequence if present on the same individual chromosome (i.e. chromosome of either maternal or paternal origin), because the other copy of the gene product will remain functional. On the other hand, if one of the inactivating mutations is present in the maternal chromosome and the other in the paternal chromosome, there is no functional copy of the gene product, resulting in a negative phenotype (non-viability, increased risk for disease and others). Haplotyping is also used to predict risk or susceptibility to specific genetic diseases, as many genetic associations are tied to haplotypes. For example, the various haplotypes of the human leukocyte antigen (HLA) system are associated with genetic diseases ranging from autoimmune disease to cancers.

Another instance in which phasing information is useful is distinguishing between functional genes and their non-functional pseudogene counterparts within the genome. One well known functional gene/pseudogene pair is the genes SMN1 and SMN2, which differ in sequence by only five nucleotides over many Kb of sequence, yet one of the nucleotide differences renders the SMN2 gene almost completely non-functional. Using short read sequencing, a mutation may be found in one of the two genes, but unless the mutation happens to occur within the sequencing read that also covers one of the known nucleotide differences between SMN1 and SMN2, it will be impossible to know which of the genes (the functional gene, or the nonfunctional pseudogene) is mutated.

The present NGS methods employ short read sequencing to query regions of variable DNA sequence (polymorphisms etc.) interspersed within regions of conserved DNA sequence. As significant blocks of conserved sequence are typically interspersed between the variable regions, short read sequencing does not lend itself to phasing analysis. Although methods have been developed to obtain phasing information, these methods (for example, Sanger sequencing and subcloning), are typically labor intensive and/or costly.

There is a need for improved NGS methods that provide phasing information. Such methods would ideally provide a highly parallel platform for performing multiple sequencing reactions from the same immobilized templates. The invention described herein fulfills this need.

SUMMARY OF THE INVENTION

The present invention provides novel methods, compositions and kits for phasing two or more nucleic acid sequences in a sample. Specifically, an important aspect of this invention is the methods and compositions that allow for determining whether two or more nucleic acid sequences (typically comprising regions of sequence variation) are located on the same nucleic acid template, such as a chromosome or a chromosomal fragment. The methods and compositions of the invention can also be used to distinguish and differentiate between two closely related nucleic acid sequences by compiling and aligning data from sequential sequencing reads.

The methods, kits and compositions of the present invention employ sequential paired sequencing reads from the same immobilized nucleic acid template. The reads are generated by successive rounds of priming, sequencing, denaturing and repriming, and the results from multiple reads originating from the same template are compiled to obtain phasing information.

Additionally, the methods, kits and compositions of the present invention employ pools of oligonucleotides used as priming sites in sequencing by synthesis reactions that target specific regions of specific DNAs for sequencing. These oligonucleotide pools can be used onboard a sequencer to extend the sequencing of DNAs that have already undergone first round of sequencing.

In one aspect, the invention provides a method for relating multiple nucleic acid sequences (typically comprising regions of sequence variation) to the same nucleic acid template. In some embodiments, the method comprises: a) creating a directional nucleic acid library; b) sequencing the library with an oligonucleotide primer; c) denaturing the first strand; d) performing a second round of sequencing by introducing a new oligonucleotide primer containing sequence complementary to conserved regions present in some of the nucleic acid templates within the nucleic acid library; e) repeating steps c) and d) as needed; and f) compiling sequencing data from the successive sequencing reads to differentiate between closely related nucleic acid sequences.

In some embodiments, the directional nucleic acid library comprises closely related nucleic acid sequences as inserts. In some embodiments, the conserved regions within the nucleic acid inserts are located adjacent to variable regions. In some embodiments, alignment of multiple variable regions enables differentiating between and/or typing of related transcripts. In some embodiments, alignment of multiple variable regions enables differentiating between and/or typing of related micro-organisms.

In another aspect, the invention provides a method for differentiating between closely related nucleic acid sequences (such as genes and pseudogenes) by using specific-sets of oligonucleotide primers containing sequence complementary to a common region shared by the closely related sequences. In some embodiments, the method comprises: a) creating a directional sequencing library with closely related nucleic acid sequences as inserts; b) sequencing the library with an oligonucleotide primer; c) denaturing the first strand; d) performing a second round of sequencing by introducing a new oligonucleotide primer containing sequence complementary to conserved regions present in some of the nucleic acid templates within the nucleic acid library; e) repeating steps c) and d) as needed; and f) compiling sequencing data from the successive sequencing reads to differentiate between closely related nucleic acid sequences.

Kits for performing any of the methods described herein are another feature of the invention. Such kits may include reagents, enzymes and platforms for amplification and sequencing of nucleic acids. In one embodiment, a kit is provided comprising: a) an adaptor or several adaptors, b) one or more of oligonucleotide primers, and c) reagents for amplification. In another embodiment, the kit further comprises reagents for sequencing. A kit will preferably include instructions for employing the kit components as well as the use of any other reagent not included in the kit.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

The novel features of the invention are set forth with particularity in the appended claims. A better understanding of the features and advantages of the present invention will be obtained by reference to the following description that sets forth illustrative embodiments, in which the principles of the invention are utilized, and the accompanying drawings of which:

DETAILED DESCRIPTION OF THE INVENTION

General

Figure 1:
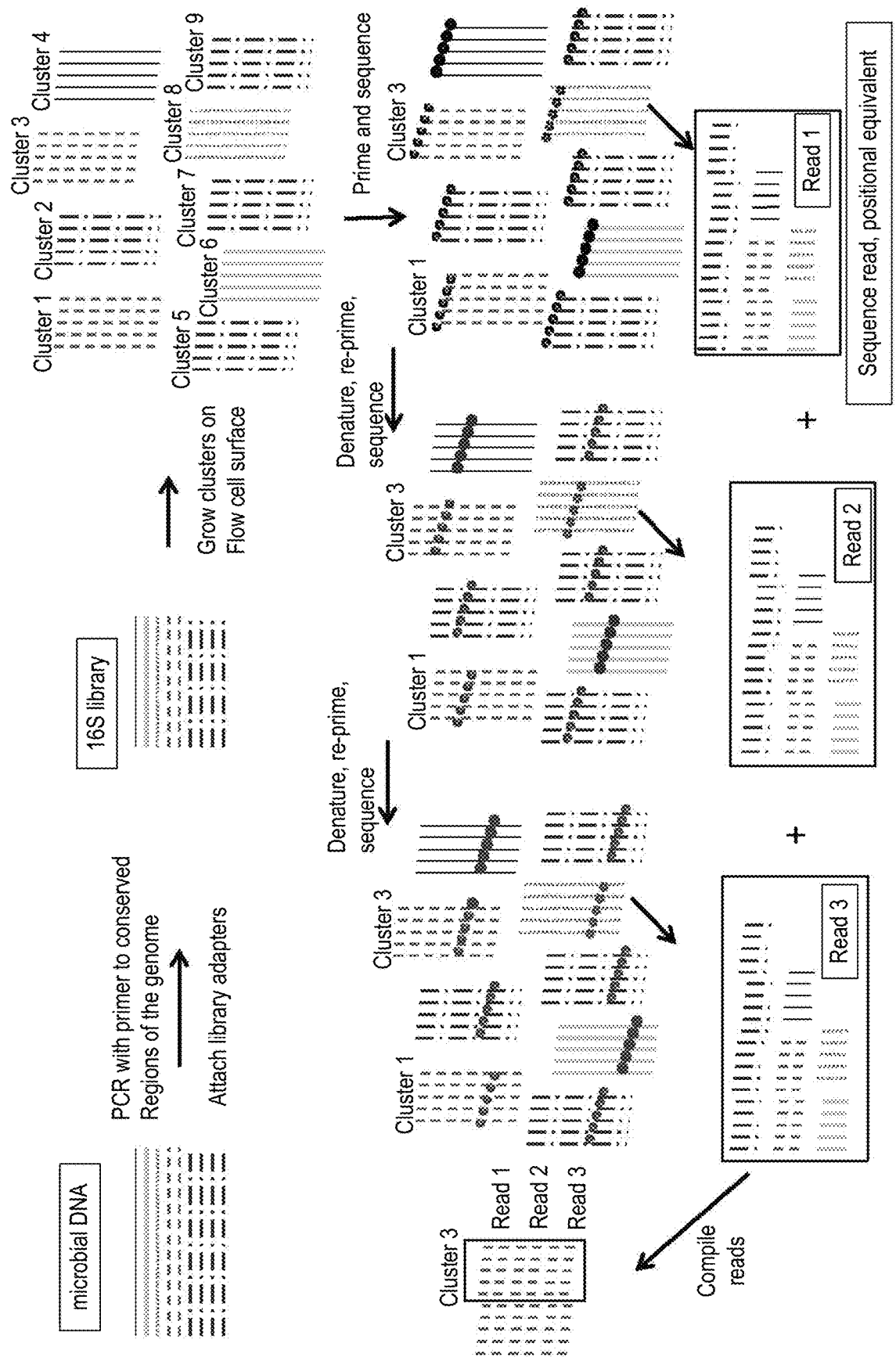
FIG. 1 depicts sequential sequencing method as applied to 16S microbial rRNA characterization, as described in Example 1.
Figure 2:
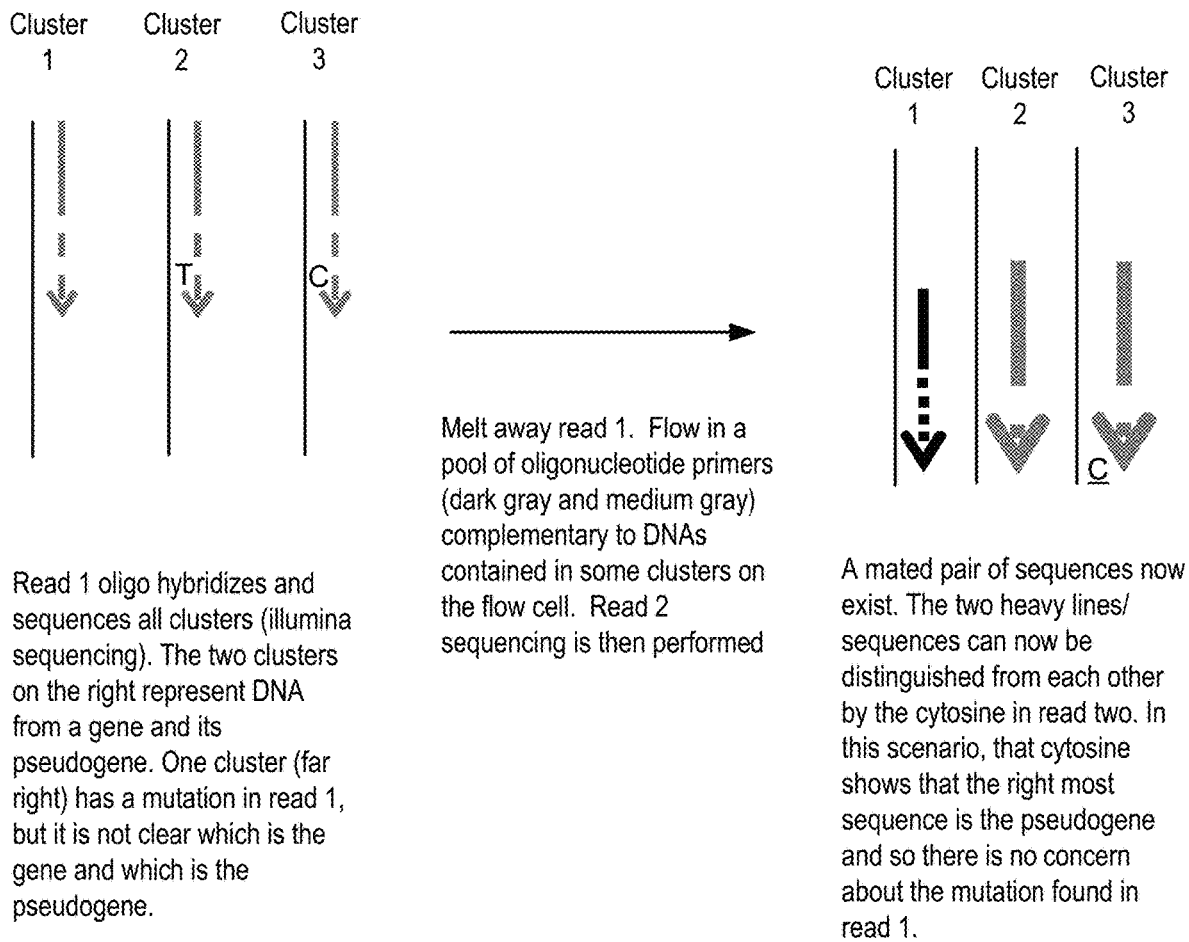
FIG. 2 depicts the use of specific oligonucleotide pools and the generation of mated pairs of sequencing reads to differentiate between two closely related nucleotide sequences, such as a gene/pseudogene pair.

The methods of the invention can be used for determining whether two or more nucleic acid sequences (typically comprising regions of variable sequence) in a sample are located on the same nucleic acid template, such as a chromosome or a chromosomal fragment. The methods of the invention can be further used to differentiate between closely related nucleic acid sequences. Such methods are useful, for example, for haplotyping, SNP phasing, determining downstream exons in RNA-seq, and in genetic diagnostics applications. The methods, kits and compositions of the present invention employ sequential paired sequencing reads from the same immobilized nucleic acid template. Altogether, the methods of the present invention provide an improvement over the existing methods by offering a highly parallel, efficient method for obtaining phasing information.

Reference will now be made in detail to exemplary embodiments of the invention. While the disclosed methods and compositions will be described in conjunction with the exemplary embodiments, it will be understood that these exemplary embodiments are not intended to limit the invention. On the contrary, the invention is intended to encompass alternatives, modifications and equivalents, which may be included in the spirit and scope of the invention.

Unless otherwise specified, terms and symbols of genetics, molecular biology, biochemistry and nucleic acid used herein follow those of standard treatises and texts in the field, e.g. Kornberg and Baker, *DNA Replication*, Second Edition (W.H. Freeman, N.Y., 1992); Lehninger, *Biochemistry*, Second Edition (Worth Publishers, New York, 1975); Strachan and Read, Human *Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like.

Phasing and Haplotype

As used herein, the term "phasing" refers to the process of determining whether two or more nucleic acid sequences (typically comprising regions of sequence variation) are located on the same nucleic acid template, such as a chromosome or a chromosomal fragment. Phasing may refer to resolving two or more single-nucleotide variants or polymorphisms within a single sequencing read. Alternatively, phasing may refer to resolving sequencing data over a large genomic region, or resolving a whole genome sequence.

As used herein, the term "haplotype" refers to the pattern of alleles within each individual chromosome. Alternatively, haplotype may refer to a set of single-nucleotide polymorphisms (SNPs) that are linked or present together on a single chromosome. The term haplotype may be used to refer to as few as two alleles or SNPs that are linked or present together on a single chromosome.

Oligonucleotides of the Invention

As used within the invention, the term "oligonucleotide" refers to a polynucleotide chain, typically less than 200 residues long, most typically between 15 and 100 nucleotides long, but also intended to encompass longer polynucleotide chains. Oligonucleotides may be single- or double-stranded. The terms "oligonucleotide probe" or "probe", as used in this invention, refer to an oligonucleotide capable of hybridizing to a complementary nucleotide sequence. As used in this invention, the term "oligonucleotide" may be used interchangeably with the terms "primer", "adaptor" and "probe".

As used herein, the terms "hybridization"! "hybridizing" and "annealing" are used interchangeably and refer to the pairing of complementary nucleic acids.

The term "primer", as used herein, refers to an oligonucleotide, generally with a free 3' hydroxyl group, that is capable of hybridizing with a template (such as a target polynucleotide, target DNA, target RNA or a primer extension product) and is also capable of promoting polymerization of a polynucleotide complementary to the template. A primer may contain a non-hybridizing sequence that constitutes a tail of the primer. A primer may still be hybridizing to a target even though its sequences are not fully complementary to the target.

The primers of the invention are generally oligonucleotides that are employed in an extension reaction by a polymerase along a polynucleotide template, such as in PCR or cDNA synthesis, for example. The oligonucleotide primer is often a synthetic polynucleotide that is single stranded, containing a sequence at its 3'-end that is capable of hybridizing with a sequence of the target polynucleotide. Normally, the 3' region of the primer that hybridizes with the target nucleic acid has at least 80%, preferably 90%, more preferably 95%, most preferably 100%, complementarity to a sequence or primer binding site.

"Complementary", as used herein, refers to complementarity to all or only to a portion of a sequence. The number of nucleotides in the hybridizable sequence of a specific oligonucleotide primer should be such that stringency conditions used to hybridize the oligonucleotide primer will prevent excessive random non-specific hybridization. Usually, the number of nucleotides in the hybridizing portion of the oligonucleotide primer will be at least as great as the defined sequence on the target polynucleotide that the oligonucleotide primer hybridizes to, namely, at least 5, at least 6, at least 7, at least 8, at least 9, at least 10, at least 11, at least 12, at least 13, at least 14, at least 15, at least about 20, and generally from about 6 to about 10 or 6 to about 12 of 12 to about 200 nucleotides, usually about 10 to about 50 nucleotides. In general, the target polynucleotide is larger than the oligonucleotide primer or primers as described previously.

In some cases, the identity of the investigated target polynucleotide sequence is known, and hybridizable primers can be synthesized precisely according to the antisense sequence of the aforesaid target polynucleotide sequence. In other cases, when the target polynucleotide sequence is unknown, the hybridizable sequence of an oligonucleotide primer is a random sequence. Oligonucleotide primers comprising random sequences may be referred to as "random primers", as described below. In yet other cases, an oligonucleotide primer such as a first primer or a second primer comprises a set of primers such as for example a set of first primers or a set of second primers. In some cases, the set of first or second primers may comprise a mixture of primers designed to hybridize to a plurality (e.g. 2, 3, 4, about 6, 8, 10, 20, 40, 80, 100, 125, 150, 200, 250, 300, 400, 500, 600, 800, 1000, 1500, 2000, 2500, 3000, 4000, 5000, 6000, 7000, 8000, 10,000, 20,000, 25,000 or more) of target sequences. In some cases, the plurality of target sequences may comprise a group of related sequences, random sequences, a whole transcriptome or fraction (e.g. substantial fraction) thereof, or any group of sequences such as mRNA.

In some embodiments of the invention, random priming is used. A "random primer", as used herein, is a primer that generally comprises a sequence that is not designed based on a particular or specific sequence in a sample, but rather is based on a statistical expectation (or an empirical observation) that a sequence of the random primer is hybridizable, under a given set of conditions, to one or more sequences in a sample. A random primer will generally be an oligonucleotide or a population of oligonucleotides comprising a random sequence(s) in which the nucleotides at a given position on the oligonucleotide can be any of the four nucleotides A, T, G, C or any of their analogs. A random primer may comprise a 5' or 3' region that is a specific, non-random sequence. In some embodiments of the invention, the random primers comprise tailed primers with a 3' random sequence region and a 5' non-hybridizing region that comprises a specific, common adaptor sequence. The sequence of a random primer, or its complement, may or may not be naturally occurring, and may or may not be present in a pool of sequences in a sample of interest. A "random primer" can also refer to a primer that is a member of a population of primers (a plurality of random primers) which are collectively designed to hybridize to a desired target sequence or sequences.

In some embodiments of the invention, standard or universal sequencing primers are used. In some embodiments of the invention, sequence-specific primers that hybridize to a conserved region or conserved regions within the nucleic acid inserts in the sequencing library are used. In some embodiments of the invention, the sequence-specific primers are designed to hybridize to conserved regions adjacent to regions of variable sequence within the nucleic acid inserts, thereby enabling differentiating between closely related sequences. In some embodiments of the invention, a set of oligonucleotide primers that hybridize to sequences shared in closely related sequences, such as gene/pseudogene pairs, are used.

The term "adaptor", as used herein, refers to an oligonucleotide of known sequence, the ligation of which to a target polynucleotide or a target polynucleotide strand of interest enables the generation of amplification-ready products of the target polynucleotide or the target polynucleotide strand of interest. Various adaptor designs are envisioned. Various ligation processes and reagents are known in the art and can be useful for carrying out the methods of the invention. For example, blunt ligation can be employed. Similarly, a single dA nucleotide can be added to the 3'-end of the double-stranded DNA product, by a polymerase lacking 3'-exonuclease activity and can anneal to an adaptor comprising a dT overhang (or the reverse). This design allows the hybridized components to be subsequently ligated (e.g., by T4 DNA ligase). Other ligation strategies and the corresponding reagents and known in the art and kits and reagents for carrying out efficient ligation reactions are commercially available (e.g, from New England Biolabs, Roche).

Input Nucleic Acid

The input is a nucleic acid. The input nucleic acid can be DNA, or complex DNA, for example genomic DNA. The input DNA may also be cDNA. The cDNA can be generated from RNA, e.g., mRNA. The input DNA can be of a specific species, for example, human, rat, mouse, other animals, specific plants, bacteria, algae, viruses, and the like. The input complex also can be from a mixture of genomes of different species such as host-pathogen, bacterial populations and the like. The input DNA can be cDNA made from a mixture of genomes of different species. Alternatively, the input nucleic acid can be from a synthetic source. The input DNA can be mitochondrial DNA. The input DNA can be cell-free DNA. The cell-free DNA can be obtained from, e.g., a serum or plasma sample. The input DNA can comprise one or more chromosomes. For example, if the input DNA is from a human, the DNA can comprise one or more of chromosome 1, 2, 3, 4, 5, 6, 7, 8, 9, 10, 11, 12, 13, 14, 15, 16, 17, 18, 19, 20, 21, 22, X, or Y. The DNA can be from a linear or circular genome. The DNA can be plasmid DNA, cosmid DNA, bacterial artificial chromosome (BAC), or yeast artificial chromosome (YAC). The input DNA can be from more than one individual or organism. The input DNA can be double stranded or single stranded. The input DNA can be part of chromatin. The input DNA can be associated with histones.

Directional Library Construction

The term "strand specific" or "directional", as used herein, refers to the ability to differentiate in a double-stranded polynucleotide between the original template strand and the strand that is complementary to the original template strand.

In some embodiments, the methods of the invention contemplate preserving information about the direction of single-stranded nucleic acid molecules while generating double-stranded polynucleotides. One of the strands of the double-stranded polynucleotide is synthesized so that it has at least one modified nucleotide incorporated into it along the entire length of the strand. In some embodiments, the incorporation of the modified nucleotide marks the strand for degradation or removal.

In some embodiments, the methods of the invention contemplate construction of directional nucleic acid libraries as described in pending U.S. application Ser. No. 13/643,056, titled COMPOSITIONS AND METHODS FOR DIRECTIONAL NUCLEIC ACID AMPLIFICATION AND SEQUENCING, Ser. No. 13/643,056.

Methods of Amplification

Methods of amplification are well known in the art. In some embodiments, the amplification is exponential, e.g. in the enzymatic amplification of specific double stranded sequences of DNA by a polymerase chain reaction (PCR). In other embodiments the amplification method is linear. In other embodiments the amplification method is isothermal.

Methods of Sequencing

The methods of the invention contemplate sequential sequencing of directional NGS libraries. Sequencing methods are also well known in the art.

For example, a sequencing technique that can be used in the methods of the provided invention is the method commercialized by Illumina, as described U.S. Pat. Nos. 5,750,341; 6,306,597; and 5,969,119. Directional (strand-specific) libraries are prepared, and the selected single-stranded nucleic acid is amplified, for example, by PCR. The resulting nucleic acid is then denatured and the single-stranded amplified polynucleotides are randomly attached to the inside surface of flow-cell channels. Unlabeled nucleotides are added to initiate solid-phase bridge amplification to produce dense clusters of double-stranded DNA. To initiate the first base sequencing cycle, four labeled reversible terminators, primers, and DNA polymerase are added. After laser excitation, fluorescence from each cluster on the flow cell is imaged. The identity of the first base for each cluster is then recorded. Cycles of sequencing are performed to determine the fragment sequence one base at a time.

In some embodiments, the methods of the present invention may employ sequencing by ligation methods commercialized by Applied Biosystems (e.g., SOLiD sequencing). In other embodiments, the methods of the present invention may employ sequencing by synthesis using the methods commercialized by 454/Roche Life Sciences, including but not limited to the methods and apparatus described in Margulies et al., Nature (2005) 437:376-380 (2005); and U.S. Pat. Nos. 7,244,559; 7,335,762; 7,211,390; 7,244,567; 7,264,929; and 7,323,305. In other embodiments, the methods of the present invention may employ the sequencing methods commercialized by Helicos BioSciences Corporation (Cambridge, Mass.) as described in U.S. application Ser. No. 11/167,046, and U.S. Pat. Nos. 7,501,245; 7,491,498; 7,276,720; and in U.S. Patent Application Publication Nos. US20090061439; US20080087826; US20060286566; US20060024711; US20060024678; US20080213770; and US20080103058. In other embodiments, the methods of the present invention may employ sequencing by the methods commercialized by Pacific Biosciences as described in U.S. Pat. Nos. 7,462,452; 7,476,504; 7,405,281; 7,170,050; 7,462,468; 7,476,503; 7,315,019; 7,302,146; 7,313,308; and US Application Publication Nos. US20090029385; US20090068655; US20090024331; and US20080206764.

Another example of a sequencing technique that can be used in the methods of the provided invention is nanopore sequencing (see e.g. Soni G V and Meller A. (2007) Clin Chem 53: 1996-2001). A nanopore can be a small hole of the order of 1 nanometer in diameter. Immersion of a nanopore in a conducting fluid and application of a potential across it can result in a slight electrical current due to conduction of ions through the nanopore. The amount of current that flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore can represent a reading of the DNA sequence.

Another example of a sequencing technique that can be used in the methods of the provided invention is semiconductor sequencing provided by Ion Torrent (e.g., using the Ion Personal Genome Machine (PGM)). Ion Torrent technology can use a semiconductor chip with multiple layers, e.g., a layer with micro-machined wells, an ion-sensitive layer, and an ion sensor layer. Nucleic acids can be introduced into the wells, e.g., a clonal population of single nucleic can be attached to a single bead, and the bead can be introduced into a well. To initiate sequencing of the nucleic acids on the beads, one type of deoxyribonucleotide (e.g., dATP, dCTP, dGTP, or dTTP) can be introduced into the wells. When one or more nucleotides are incorporated by DNA polymerase, protons (hydrogen ions) are released in the well, which can be detected by the ion sensor. The semiconductor chip can then be washed and the process can be repeated with a different deoxyribonucleotide. A plurality of nucleic acids can be sequenced in the wells of a semiconductor chip. The semiconductor chip can comprise chemical-sensitive field effect transistor (chemFET) arrays to sequence DNA (for example, as described in U.S. Patent Application Publication No. 20090026082). Incorporation of one or more triphosphates into a new nucleic acid strand at the 3' end of the sequencing primer can be detected by a change in current by a chemFET. An array can have multiple chemFET sensors.

Kits

Any of the compositions described herein may be comprised in a kit. In a non-limiting example, the kit, in a suitable container, comprises: an adaptor or several adaptors, one or more of oligonucleotide primers and reagents for ligation, primer extension and amplification. The kit may also comprise means for purification, such as a bead suspension, and nucleic acid modifying enzymes.

Products based on the Methods of the Invention

Products based on the methods of the invention may be commercialized by the Applicants under the Encore® Complete family. Encore is a registered trademark of NuGEN Technologies, Inc.

EXAMPLES

Example 1—Characterization of the Human Oral Microbiome by Sequential Sequencing of Bacterial 16S Ribosomal DNA This example describes the characterization of the human oral microbiome by sequencing of the 16S rRNA gene sequences of a number of related bacterial organisms. 16S rRNA gene sequences contain species-specific hypervariable regions that can provide means for bacterial identification.

Sample Nucleic Acid

Microbial genomic DNA is isolated from human saliva using the OMNIgene-DISCOVER sample collection kit (DNA Genotek) according to the manufacturer's instructions. Extracted DNA is then fragmented via sonication to an average length of 400 bp and purified using Agencourt AMPure XP beads (Beckman Coulter Genomics).

Generation of Control and Test 16 S Libraries with Ligated Adapters

The NuGEN Ovation Ultralow Library System (NuGEN Technologies) is used to generate two directional next generation sequencing libraries from 100 ng of the purified sample according to manufacturer's instructions.

Ligation products of at least 100 bp in length are purified by selective binding to Agencourt AMPure XP beads.

Cyclic Primer Sequencing

16 S ribosomal DNA fragments from the test library are sequenced by Illumina sequencing system using standard forward primers. Alternatively, a custom primer may be used. Following the first sequencing read, the DNA is denatured to wash away the first strand. A second primer that hybridizes to conserved regions within the 16 S library inserts is injected into the sequencer to act as a priming site for a second sequencing read. This second primer is designed to hybridize to conserved regions that are adjacent to variable regions within the inserts. Successive rounds of denaturation, re-priming and sequencing are performed with primers that hybridize to additional conserved regions. Sequence reads from successive priming and sequencing are compiled and aligned to map reads originating from the same nucleic acid fragments.

Example 2—Genomic DNA Sequencing—Distinguishing Between the SMN1 Gene and SMN2 Pseudogene Using Sequential Sequencing Genomic DNA sequencing libraries are made using the NuGEN's Encore system. These libraries are sequenced on a DNA sequencing system such as those made by Illumina, Ion Torrent, Pacific Biosciences, or Complete Genomics. Following a first sequencing read, the DNA is denatured to wash away the first strand. A pool of primers that hybridize to common sequences in gene/pseudogene pairs are injected into the sequencer to act as a priming site for a second sequencing read. A primer set may include primers that will sequence through one of the nucleotide differences between SMN1 and SMN2 as well as primers that will generate sequence to read nucleotide differences, and therefore determine whether a sequencing read is from a globin gene or pseudogene. A combination of such primers will allow multiple gene/pseudogene pairs across the genome to be analyzed simultaneously for genetic mutations.

Example 3—Targeted DNA Sequencing Library

A targeted DNA sequencing library is made using the a target enrichment product from NuGEN, Agilent, Illumina, or Nimblegen. These libraries are sequenced on a DNA sequencing system such as those made by Illumina, Ion Torrent, Pacific Biosciences, or Complete Genomics. Following a first sequencing read, the DNA is denatured to wash away the first strand. A pool of primers that hybridize to common sequences in gene/pseudogene pairs are injected into the sequencer to act as a priming site for a second sequencing read. A primer set may include primers that will sequence through one of the nucleotide differences between SMN1 and SMN2 as well as primers that will generate sequence to read nucleotide differences, and therefore determine whether a sequencing read is from a globin gene or pseudogene. A combination of such primers will allow multiple gene/pseudogene pairs across the genome to be analyzed simultaneously for genetic mutations. This type of technology is useful for genetic diagnostics.

Example 4—RNA-Sequencing Library

An RNA sequencing library is made from NuGEN's Encore Complete RNA-Seq Library System. The library is sequenced on an Illumina DNA sequencer. Following the first sequencing read, a pool of primers that will hybridize to specific exons of interest is injected into the sequencing machine. These primers are used to generate a second sequencing read in a downstream exon. The second, targeted sequencing read provides information about which exons have been spliced together to generate a particular RNA transcript.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for relating at least two nucleic acid sequences or regions of sequence variation to the same nucleic acid template, the method comprising:
   a. creating a strand-oriented nucleic acid library comprising nucleic acid from a chromosome;
   b. sequencing a template immobilized on a solid support within the strand-oriented library with an oligonucleotide primer;
   c. denaturing strands of nucleic acid fragments in the library;
   d. annealing a new oligonucleotide primer to the template that is complementary to a conserved region or conserved regions within the chromosome; and
   e. sequencing the template within the nucleic acid library with the new oligonucleotide primer to thereby generate multiple nucleic acid sequence reads from the same template,
   wherein the sequencing steps proceed via template-dependent sequencing-by-synthesis reactions.

2. The method of claim 1, wherein the nucleic acid libraries are amplicons originating from conserved regions of sequence.

3. The method of claim 2, wherein the conserved regions are adjacent to variable regions.

4. The method of claim 3, wherein alignment of multiple variable regions enables differentiation and/or typing of related transcripts.

5. The method of claim 3, wherein alignment of multiple variable regions enables differentiation and/or typing of related micro-organisms.

6. The method of claim 1, wherein libraries are reduced complexity.

7. The method of claim 6, wherein reduced complexity is achieved by target capture.

8. A method for distinguishing between two closely related nucleic acid sequences, the method comprising:
   a. creating a strand-oriented nucleic acid library with closely related nucleic acid sequences from one or more chromosomes as inserts;
   b. sequencing a template immobilized on a solid support within the strand-oriented library with a first primer;
   c. denaturing strands of nucleic acid fragments in the library;
   d. annealing a second primer to a conserved region in an insert of the template; and
   e. sequencing the template with the second primer to thereby generate multiple nucleic acid sequence reads from the same template,
   wherein the sequencing steps proceed via template-dependent sequencing-by-synthesis reactions.

9. A sequencing method comprising:
   creating a nucleic acid library comprising a template strand from a chromosome;
   sequencing the template strand immobilized on a solid support with a first primer to produce a first sequence read;
   denaturing a fragment comprising the template strand; and
   sequencing the template strand with a second primer that is complementary to a conserved region within the chromosome to produce a second sequence read to thereby generate the first sequence read and the second sequence read from the template strand,
   wherein the sequencing steps proceed via template-dependent sequencing-by-synthesis reactions.

10. The method of claim 9, wherein the conserved region is found in both members of a gene/pseudogene pair.

11. The method of claim 9, wherein the conserved region is found in SMN1 and SMN2.

* * * * *